(12) United States Patent
Mak et al.

(10) Patent No.: US 11,666,410 B2
(45) Date of Patent: *Jun. 6, 2023

(54) DEFORMABLE AND SHAPE-ABLE SURGICAL LIGHTING DEVICE AND SYSTEM

(71) Applicant: SYNAPTIVE MEDICAL INC., Toronto (CA)

(72) Inventors: Siu Wai Jacky Mak, Toronto (CA); Michael Frank Gunter Wood, Toronto (CA)

(73) Assignee: Synaptive Medical Inc.

( * ) Notice: Subject to any disclaimer, the term of this patent is extended or adjusted under 35 U.S.C. 154(b) by 72 days.

This patent is subject to a terminal disclaimer.

(21) Appl. No.: 17/304,180

(22) Filed: Jun. 16, 2021

(65) Prior Publication Data

US 2021/0307860 A1    Oct. 7, 2021

Related U.S. Application Data

(63) Continuation of application No. 14/899,254, filed as application No. PCT/CA2015/050243 on Mar. 27, 2015, now Pat. No. 11,076,930.

(51) Int. Cl.
| | |
|---|---|
| *A61B 90/30* | (2016.01) |
| *A61B 1/07* | (2006.01) |
| *A61B 1/06* | (2006.01) |
| *A61B 5/00* | (2006.01) |
| *A61B 17/00* | (2006.01) |
| *A61B 34/20* | (2016.01) |

(52) U.S. Cl.
CPC ............ *A61B 90/30* (2016.02); *A61B 1/0638* (2013.01); *A61B 1/07* (2013.01); *A61B 5/0071* (2013.01); *A61B 5/0075* (2013.01); *A61B 5/0084* (2013.01); *A61B 2017/00946* (2013.01); *A61B 2034/2055* (2016.02); *A61B 2090/306* (2016.02)

(58) Field of Classification Search
None
See application file for complete search history.

(56) References Cited

U.S. PATENT DOCUMENTS

| | | | | |
|---|---|---|---|---|
| 2004/0204651 A1* | 10/2004 | Freeman | ............... | A61B 5/0075 600/478 |
| 2012/0078046 A1* | 3/2012 | Sasaki | ............. | A61B 1/000094 600/109 |

* cited by examiner

*Primary Examiner* — Katherine L Fernandez

(57) ABSTRACT

A conductor-less, shape-able, surgical lighting system and methods for use in surgical applications in which a medical clinician, once having established a surgical site, can shape the lighting system to selectively illuminate desired volumes of the surgical site. The system includes preselected lengths of an elongate light emitting member formed of a transparent elastomer matrix material having a glass transition temperature of lower than or substantially equal to room temperature to render the elongate light emitting member bendable and shape-able. Embedded in the transparent elastomer matrix material are particles of a transparent material having a refractive index different from a refractive index of the matrix material dispersed in the elastomer matrix material so that light coupled into the elongate light emitting member is scattered and refracted out of the elongate light emitting member along its length. One end of the elongate light emitting member is coupled with a light source.

20 Claims, 15 Drawing Sheets

* # DEFORMABLE AND SHAPE-ABLE SURGICAL LIGHTING DEVICE AND SYSTEM

CROSS-REFERENCE TO RELATED APPLICATION(S)

This document is a continuation application, claiming the benefit of, and priority to, the following application(s): U.S. patent application Ser. No. 14/899,254, filed on Dec. 17, 2015, and entitled "DEFORMABLE AND SHAPE-ABLE SURGICAL LIGHTING DEVICE AND SYSTEM," and International PCT Patent Application No. PCT/CA2015/050243 filed on Mar. 27, 2015, which are hereby incorporated by reference in their entirety.

FIELD

The present disclosure relates to a clinician deformable, shape-able, light source for surgical applications.

BACKGROUND

In many current surgeries, surgical illuminator(s) is/are commonly used to provide additional lighting to the surgical field in addition to the surgical lighting, i.e. large lighting fixtures, in the operation room. Currently there are two types of related art surgical illuminators, namely standalone illuminators and tool-integrated illuminators. The standalone illuminators have a forward illumination scheme in which light shines only in the forward direction from typically the tip of the illuminator to the surgical field. When the surgeon positions the illuminator, they deliver light at a limited illumination angle and the field of illumination is typically planer. As a result, they are typically used from the side or on top of the surgical field to illuminate area that the illuminator is pointing towards. In cases when illumination of a large or deep surgical field is required, such as the case in port-based brain surgeries, these illuminators cannot illuminate the entire surgical field with enough brightness. Surgeons often have to re-position the illuminator to focus the illumination at the field of interest during the surgery. This process is cumbersome and time-consuming as the surgeon needs to re-position the illuminator constantly to observe the entire surgical field. In some cases, the surgeon also needs to drop the surgical tool in his hand to re-position the illuminator.

Examples of related art standalone illuminators are: (a) a fiber optic based surgical illuminator: http://www.synthes.com/MediaBin/US%20DATA/Product%20Support%20Materials/T-echnique%20Guides/SPTGInsightAccessRetractorJ9680B.pdf (Page 5), wherein this illuminator involves an elongated light cable enclosed by a snake tube that enables the light cable to hold its shape as it is bent, a clamp that positions the illuminator with a connector that connects to a light source through a fiber optic light cable, and an opening at the distal end of the illuminator that provides illumination in the forward scheme; and (b) a headlight: http://intl.welchallyn.com/apps/products/product.jsp?id=16-in-96-11906845-08766, wherein this headlight illuminator involves a holder that enables one to wear the illuminator on the head, an illuminator head that connects to a light source through a fiber optic light cable and a mechanical joint that fixes the illuminator head to illuminate light in the forward direction in which the user is looking.

To provide a more effective lighting solution, related art tool-integrated illuminators are developed and deliver lighting in a way that is best suited for a surgical procedure. Often, they are partly or completely integrated with the surgical tool to achieve a few goals: (1) hands-free illumination, i.e., surgeon does not have to hold a separate illuminator, (2) a more effective illumination, i.e. putting illuminator closer to the field-of-interest for more effective light delivery, and (3) a custom light field, i.e. providing an area or a way of illumination that is best suited for a surgical procedure. For example, these illuminators could be, but not limited to, a ring or a curved illuminator made for avoiding shadows and/or optimizing lighting at specific areas of the surgical field. These illuminators could also provide a forward illumination scheme that is integrated with the surgical tool. A limitation of these illuminators is that they are only suitable for certain surgical procedures since they are optimized for a surgical procedure and integrated with a specific tool. Moreover, the illumination direction and position of the illuminator is fixed with respect to the tool. These settings might not be ideal for every surgeon and cannot be adjusted to suit each surgeon's needs.

Examples of related art tool-integrated illuminators: (a) Vitom®-Ring illuminators, wherein the Vitom® is a surgical microscope that integrates fiber optic around the imaging lenses to provide illumination down toward the surgical region of interest in a forward scheme, wherein the Vitom® comprises an eyepiece that enables connection to a camera, a connector on the side that connects to a light source through a fiber optic cable, and an elongated body that comprises of lens for imaging and fiber optics around the lens for illumination; (b) Ortho-Light®: http://www.lumitex.com/medical-devices/products/ortholight/ortho-light/, wherein the Ortho-Light® is a fiber optic panel that attaches to retractors for illumination in the forward direction and in the side; and (c) retractors illumination: http://www.invuity.com/products/eikon-retractor-system/, wherein this illuminator is integrated an optical light guide in front of the retractor for illumination in mostly the downward direction.

In addition, if surgical camera is used, the color of the surgical field being displayed on the monitor changes between surgery, illuminators, and the surrounding lighting in the environment. This color often deviates from the true native color that the human eyes see and/or the preferential color that surgeons use for surgery. A spectrometer could be used to correct the color of the image being display before the surgery. However, high color precision highly depends on the actual lighting condition which changes with the type, position, shape and number of the illuminator Therefore, a needs exists for a clinician-deformable, shape-able, light source with an integrated color correction sensor which corrects the image color at the surgical field dynamically for surgical applications.

SUMMARY

The present disclosure provides a non-rigid, bendable, surgical lighting system for use in surgical applications in which a medical clinician, once having established a surgical site, can shape, by bending, the lighting system to selectively illuminate desired volumes of the surgical site.

In an embodiment, the lighting system includes one or more elongate light emitting member formed of a transparent elastomer matrix material having a glass transition temperature of lower than or substantially equal to room temperature to render the elongate light emitting member bendable and shape-able. Embedded in the transparent elastomer matrix material are particles of a transparent material having a refractive index different from a refractive index of the matrix material dispersed in the elastomer matrix material so that light coupled into the elongate light emitting member is scattered and refracted out of the elongate light emitting member along its length. A proximal end of the one or more elongate light emitting members are configured to be coupled to a light source and to a spectrometer. The length of the one or more elongate light emitting members is selected so that a medical clinician, can bend and shape it to provide a desired level of lighting of the anatomical surgical site while accommodating surgical instruments present in the anatomical surgical site. The spectrometer will connect to computer that takes the color spectrum from the spectrometer and corrects the color spectrum of the output image from a surgical camera through comparison with a standard color reference or color profiles.

The system may include one preselected length of the elongate light emitting member which is long enough to be shaped to the illuminate the desired areas of the surgical site, accounting for having to be wrapped around various surgical instruments, such as a port used during brain surgery. Alternatively, the surgical lighting system may include multiple elongate light emitting members each having an end adapted to be coupled to the light source which can be shaped independently of the other lengths. The outer surfaces of one or more sections of the elongate lengths may be masked, for example with a reflective coating, to selectively illuminate particular areas of the surgical site, with the reflective coating acting to reflect light back from the coating out of the uncoated areas to increase illumination intensity to the desired locations. The surgical lighting system may be integrated with one or more surgical tools, such as a resection tool or an access port, through a clamp on the system, or through deforming the lighting system to fit into or hold onto the tool.

A flexible, adaptive surgical lighting system comprises: (a) non-rigid, bendable surgical lighting system including one or more elongate light emitting members; (b) a light source, a proximal end of the one or more elongate light emitting members configured to be coupled to the light source; (c) a spectrometer, a computer processor connected to the spectrometer, the light source connected to the spectrometer, a camera connected to the computer processor, a visual display connected to the computer processor; (d) the spectrometer being configured to receive light reflected from an anatomical surgical site; and (e) the computer processor being programmed with instructions for: (i) receiving a reflected light intensity and color spectrum of the reflected light from the spectrometer, displaying it and to comparing it to a pre-selected color profile standard, and, based on differences between the reflected light intensity and color spectrum and the pre-selected color profile standard, adaptively adjust the light intensity and color spectrum of the displayed image; and (ii) visually displaying the adjusted light intensity and color spectrum of the light received from the anatomical surgical site, in accordance with an embodiment of the present disclosure.

A method of controlling illumination of a surgical site comprises: (a) shaping a distal end of a flexible and bendable surgical lighting member which includes one or more elongate light emitting and collecting members; (b) connecting a light source to a proximal end of the one or more elongate light emitting members, optically coupling a spectrometer to the light source, connecting a computer processor to the spectrometer, connecting a camera to the computer processor and connecting a visual display to the computer processor; (c) directing light emitted from the one or more elongate light emitting and collecting members to a surgical site and collecting light reflected from the surgical site by the one or more elongate light emitting and collecting members and directing the collected reflected light into the spectrometer; (d) directing a reflected light intensity and color spectrum of the reflected light from the spectrometer to the microprocessor and displaying it and comparing it to a pre-selected color profile standard, and, based on differences between the reflected light intensity and color spectrum and the pre-selected color profile standard, adaptively adjusting the light intensity and color spectrum of the displayed image; and (e) visually displaying the adjusted light intensity and color spectrum of the light received from the anatomical surgical site, in accordance with an embodiment of the present disclosure.

A further understanding of the functional and advantageous aspects of the present disclosure can be realized by reference to the following detailed description and drawings.

BRIEF DESCRIPTION OF THE DRAWINGS

Embodiments are described, by way of example only, with reference to the drawings, in which.

DETAILED DESCRIPTION

Figure 1:
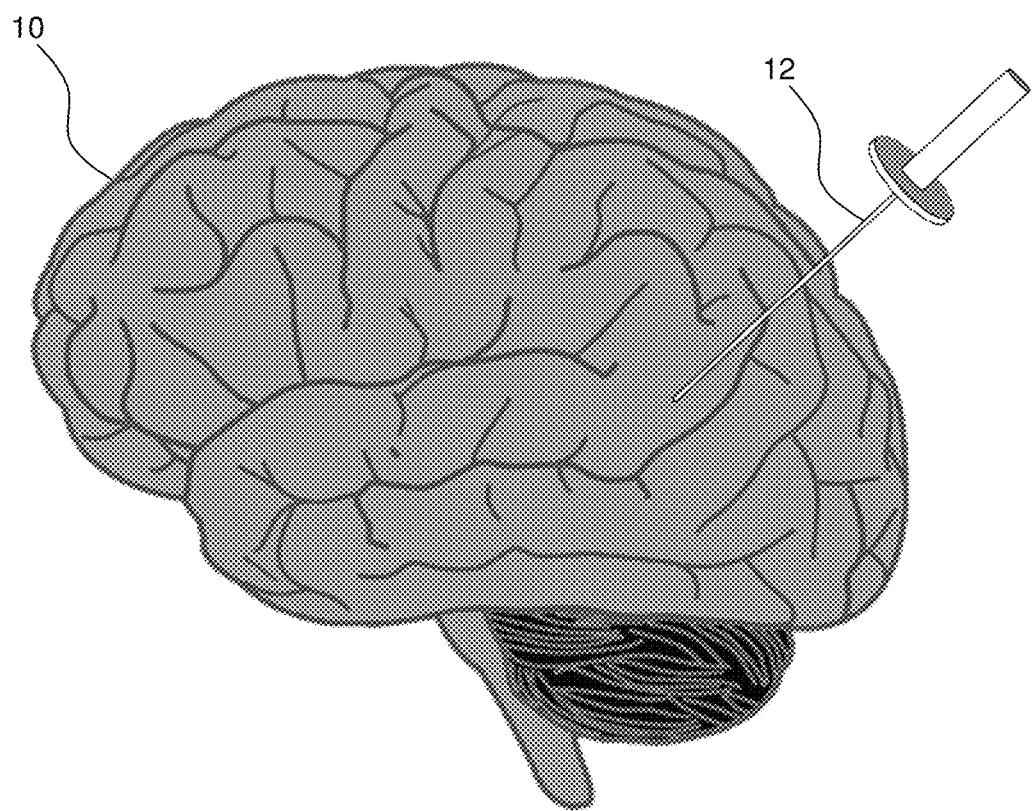
FIG. 1 is a diagram illustrating insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Various apparatuses or processes are below described to provide examples of embodiments of the disclosure. No embodiment below described limits any claimed invention; and any claimed invention may cover processes or apparatuses that differ from those below described. The claimed inventions are not limited to apparatuses or processes having all of the features of any one apparatus or process below described or to features common to multiple or all of the apparatuses or processes below described. Possible is that an apparatus or process below described is not an embodiment of any claimed invention.

Furthermore, numerous specific details are set forth in order to provide a thorough understanding of the embodiments herein described. However, understood is that the embodiments described herein may be practiced without these specific details. In other instances, well known methods, procedures and components have not been described in detail so as not to obscure the embodiments described herein. Also, the description is not to be considered as limiting the scope of the embodiments described herein.

Furthermore, in the following passages, different aspects of the embodiments are defined in more detail. In particular, any feature indicated as being preferred or advantageous may be combined with at least one other feature or features indicated as being preferred or advantageous.

Embodiments of the present disclosure provide a deformable and/or shape-able lighting system which can be shape-configured to provide desired illumination (direction, intensity and planar illumination shape) by a medical clinician. This deformable lighting system is very useful in certain types of surgery where various medical devices need to be inserted into the anatomical structures being operated on. For example, embodiments of the present lighting system are useful in minimally invasive medical procedures that are performed via an access port, whereby surgery, diagnostic imaging, therapy, or other medical procedures, e.g. minimally invasive medical procedures, are performed based on access to internal tissue through the access port, in which illumination options are limited. The present lighting system may be integrated with a resection tool, through the clamp. This enables more efficient lighting through bringing the lighting system closer to the surgical field at regions where surgeon is operating on. In another example, the present lighting system may be integrated with the access port through deforming the lighting system into a cylindrical shape. The diameter of the cylindrical shape may be made similar or smaller than the inner diameter of the access port, which enables the lighting system to be placed into the access port for illumination while leaving the center region of the access port open for surgical tool access.

An example of an access port is an intracranial conduit which may be employed in neurological procedures in order to provide access to internal tissue pathologies, such as tumors. One example of an intracranial access port is the BrainPath® surgical access port provided by NICO®, which may be inserted into the brain via an obturator with an atraumatic tip in the brain. Such an access port may be employed during a surgical procedure, by inserting the access port, via the obturator that is received within the access port, through the white matter fibers of the brain to access a surgical site.

Minimally invasive brain surgery using access ports is a recently conceived method of performing surgery on brain tumors previously considered inoperable. One object of the present disclosure is to provide a system and method to assist in minimally invasive brain surgery. To address intracranial surgical concerns, specific products such as the NICO® BrainPath® port have been developed for port-based surgery.

Referring to FIG. 1, this diagram illustrates the insertion of an access port 12 into a human brain 10, for providing access to internal brain tissue during a medical procedure, in accordance with an embodiment of the present disclosure. The access port 12 is inserted into a human brain 10, providing access to internal brain tissue. Access port 12 comprises such instruments as catheters, surgical probes, or cylindrical ports such as the NICO® BrainPath®. Surgical tools and instruments may then be inserted within the lumen of the access port 12 in order to perform surgical, diagnostic or therapeutic procedures, such as resecting tumors as necessary. The present disclosure applies equally well to catheters, deep brain stimulation (DBS) needles, a biopsy procedure, and also to biopsies and/or catheters in other medical procedures performed on other parts of the body.

Still referring to FIG. 1, in the example of a port-based surgery, a straight or linear access port 12 is typically guided down a sulci path of the brain. Surgical instruments would then be inserted down the access port 12. Optical tracking systems, used in the medical procedure, track the position of a part of the instrument that is within line-of-site of the optical tracking camera. Since the tip of the surgical instrument may be inserted within a patient, line of site to the tip of the instrument cannot always be maintained. As well, positioning the optical tracking mechanisms at the tip may be too cumbersome to be of practical use. Conventionally, the tip and orientation of the instrument is inferred through a known transformation, e.g., either measured or determined by manufactured drawings, from the visible tracked position to the tip position.

Figure 2:
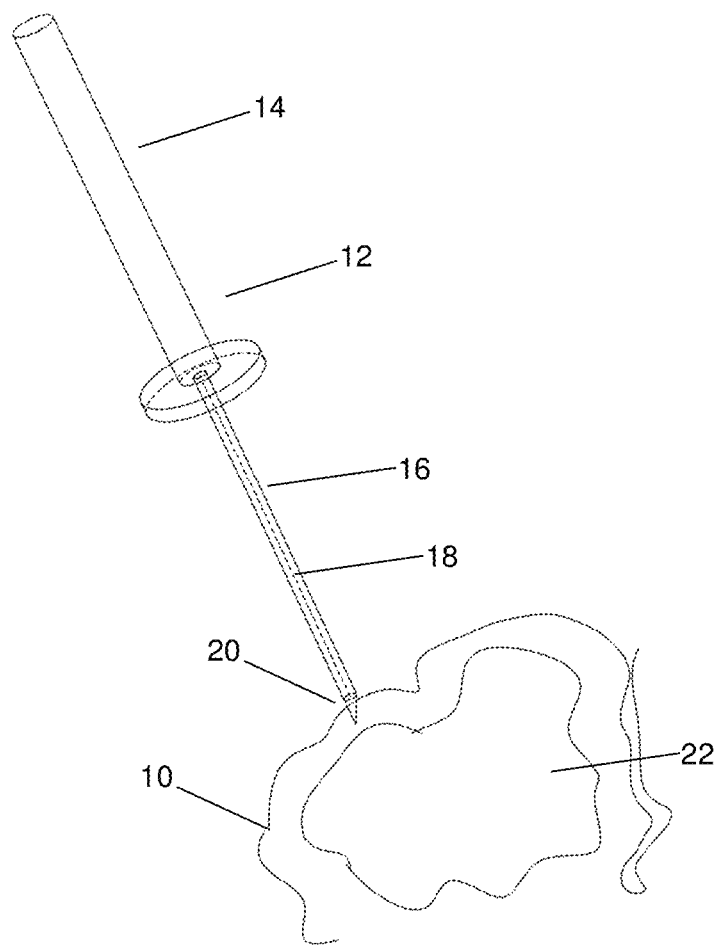
FIG. 2 is a diagram illustrating insertion of a catheter as an access port into the brain.

Referring to FIG. 2, this diagram illustrates insertion of a catheter as an access port 12 into the brain 10, in accordance with an embodiment of the present disclosure. The catheter may be used as an access port 12 positioned to navigate a human brain 10. The catheter comprises a handle 14 at its proximal end and a probe 16 at its distal end. In one example, the probe 16 is substantially straight or linear; however, curved probes could also be used. Probe 18 may be a resection tool, an image sensor and/or other types of sensing tools that can take measurements in different imaging modalities, e.g., ultrasound, Raman, optical coherence tomography (OCT), positron emission tomography (PET), magnetic resonance imaging (MRI), etc. Probe 16 may be hollow, thus, providing an internal passage 18 through which fluids or wires are passed. Probe 18 may enter the brain 10 and be navigated to targeted internal tissue 22. In one example, the probe 16 may follow sulci path 20, however, due to the typically linear nature of probe 16, a linear path to targeted internal tissue 22 is usually mapped out.

Figure 3A:
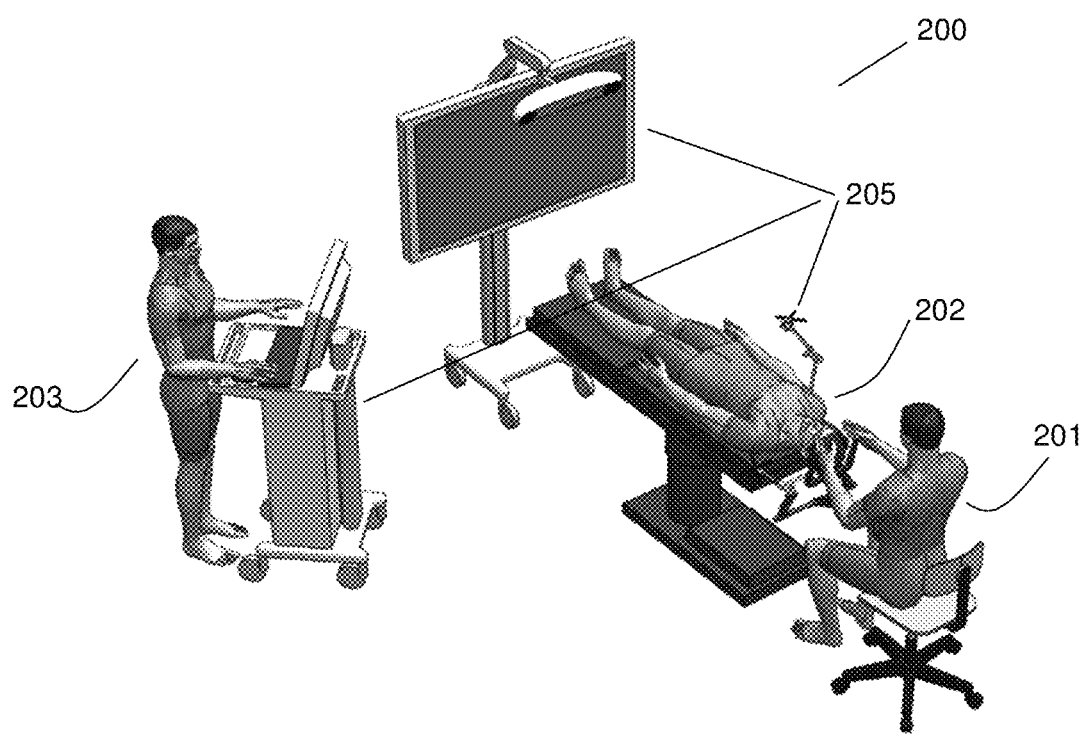
FIG. 3A is a diagram illustrating an exemplary navigation system to support minimally invasive access port-based surgery.

Referring to FIG. 3A, this diagram illustrates an exemplary navigation system environment 200 is shown, which may be used to support navigated image-guided surgery, in accordance with an embodiment of the present disclosure. A surgeon 201 conducts a surgery on a patient 202 in an operating room (OR) environment. A navigation system 205 comprising an equipment tower, tracking system, displays and tracked instruments assist the surgeon 201 during the procedure. An operator 203 is also present to operate, control and provide assistance for the navigation system 205.

Figure 3B:
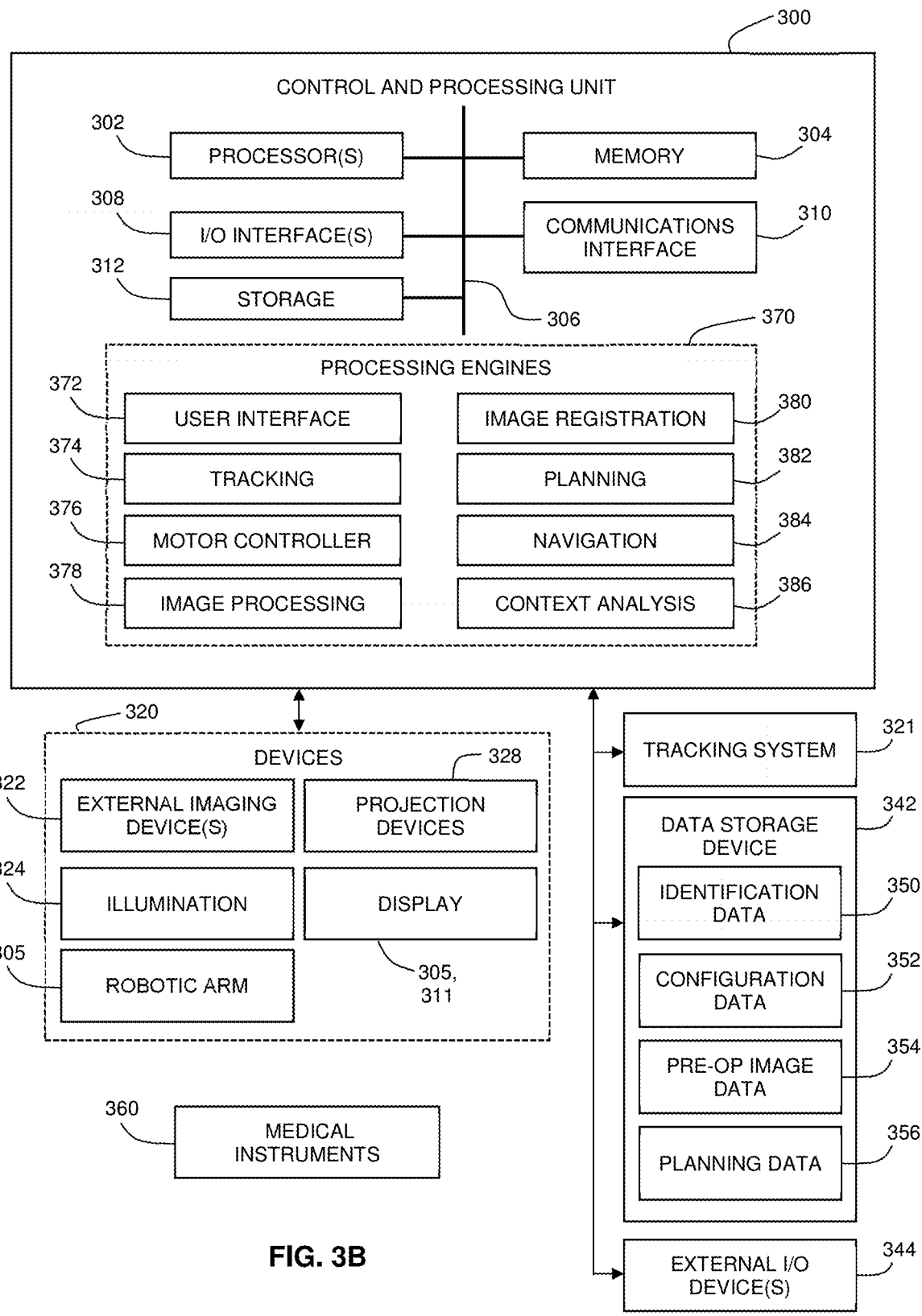
FIG. 3B is a block diagram illustrating a control and processing system usable in the navigation system, as shown in FIG. 3A.

Referring to FIG. 3B, this block diagram illustrates a control and processing system 300 that used in the navigation system environment 200, as shown in FIG. 3A, e.g., as part of the equipment tower, in accordance with an embodiment of the present disclosure. In one example, control and processing system 300 comprises one or more processors 302, a memory 304, a system bus 306, one or more input/output interfaces 308, a communications interface 310, and storage device 312. Control and processing system 300 is interfaced with other external devices, such as tracking system 321, data storage 342, and external user input and output devices 344, which comprise, for example, one or more of a display, keyboard, mouse, foot pedal, and microphone and speaker. Data storage 342 comprises any suitable data storage device, such as a local or remote computing device, e.g. a computer, hard drive, digital media device, or server), having a database stored thereon. The data storage device 342 comprises identification data 350 for identifying one or more medical instruments 360 and configuration data 352 that associates customized configuration parameters with one or more medical instruments 360. Data storage device 342 comprises preoperative image data 354 and/or medical procedure planning data 356. Although data storage device 342 is shown as a single device, in other embodiments, data storage device 342 comprises multiple storage devices.

Still referring to FIG. 3B, medical instruments 360 are identifiable by control and processing unit 300. Medical instruments 360 are coupled with, and controlled by, the control and processing unit 300, or the medical instruments 360 are operated, or otherwise employed, independent of the control and processing unit 300. Tracking system 321 is employed to track one or more of medical instruments 360 and spatially register the one or more tracked medical instruments to an intraoperative reference frame. In another example, as sheath placed over a medical instrument 360 is coupled with, and controlled by, the control and processing unit 300. The control and processing unit 300 interfaces with a number of configurable devices, and intraoperatively reconfigures one or more of such devices based on configuration parameters obtained from configuration data 352. Examples of devices 320 comprise one or more external imaging devices 322, one or more illumination devices 324, a robotic arm, one or more projection devices 328, and one or more displays 205, 211.

Still referring to FIG. 3B, exemplary aspects of the present disclosure are implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately, in one example, the processing modules 370 are stored in the memory 304 and the processing modules are collectively referred to as processing modules 370.

Still referring to FIG. 3B, the system is not intended to be limited to the components as shown. One or more components of the control and processing system 300 are provided as an external component or device. In one example, navigation module 384 is provided as an external navigation system that is integrated with control and processing system 300. Some embodiments may be implemented using processor 302 without additional instructions stored in memory 304. Some embodiments may be implemented using the instructions stored in memory 304 for execution by one or more general purpose microprocessors. Thus, the present disclosure is not limited to a specific configuration of hardware and/or software.

Still referring to FIG. 3B, while some embodiments can be implemented in fully functioning computers and computer systems, various embodiments are capable of being distributed as a computing product in a variety of forms and are capable of being applied regardless of the particular type of machine or computer readable media used to actually effect the distribution. At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device. A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Still referring to FIG. 3B, examples of computer-readable storage media include, but are not limited to, recordable and non-recordable type media such as volatile and non-volatile memory devices, read only memory (ROM), random access memory (RAM), flash memory devices; floppy and other removable disks, magnetic disk storage media, optical storage media, e.g., compact discs (CDs), digital versatile disks (DVDs), etc., among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Still referring to FIG. 3B, at least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Referring back to FIGS. 3A and 3B, according to one aspect of the present disclosure, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to other suitable medical procedures.

Figure 4A:
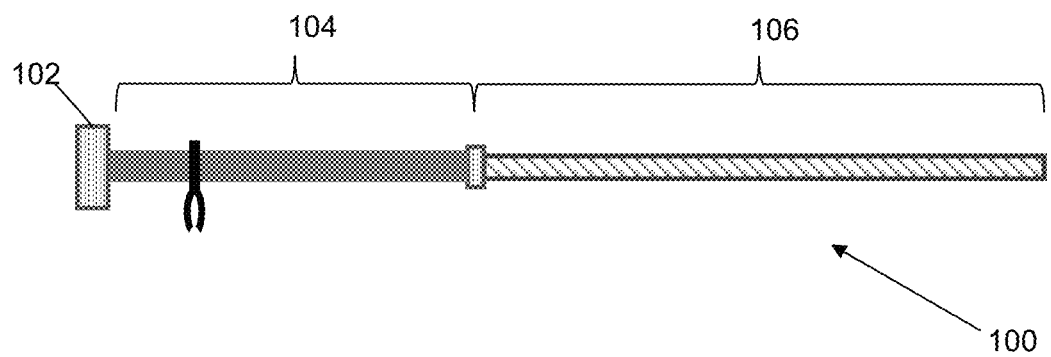
FIG. 4A is a diagram illustrating, in a side view, a deformable surgical lighting device comprising an elongate deformable illumination section for illuminating the volume of interest, a holder section which can be held by the clinician and a coupler section for coupling the lighting device to a light source, with the device fully extended and straight.
Figure 4B:
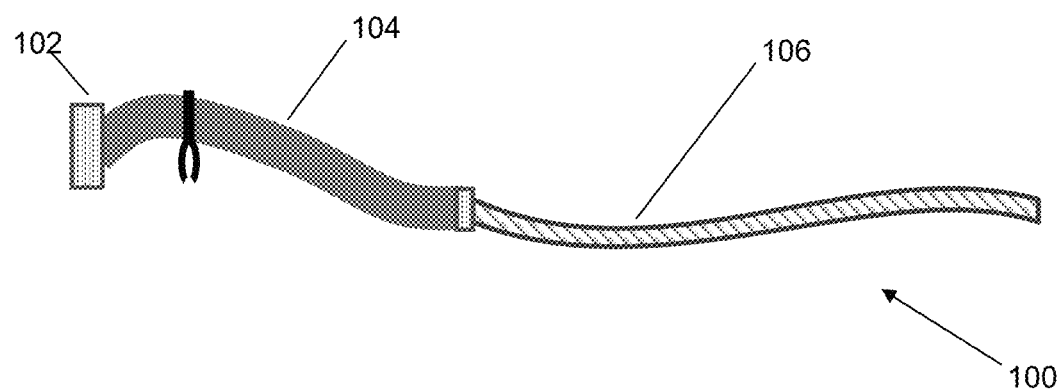
FIG. 4B is a diagram illustrating the lighting system, as shown in FIG. 4A, deformed and shaped in a nonlinear manner.

Referring to FIGS. 4A and 4B, together, these diagrams respectively illustrate a surgical illuminator 100 that provides a deformative illumination structure adaptable for different surgical procedures, operation room setups, and surgeons, in accordance with embodiments of the present disclosure. The illuminator 100 comprises a connector or optical coupling section 102 that couples with a light source, e.g. light pipe or an optical fiber bundle, or a power source. Illuminator 100 comprises a holder section 104 that enables the clinician or surgeon to control the illuminator position and illumination direction. This holder 104 is bent to hold and to position the illuminator for different surgical procedures, setups, and likings of different surgeons. This holder could also include a clamp or attachment that allows the illuminator to be held in position though attaching to other equipment in the operation room, e.g., a surgical bed.

Still referring to FIGS. 4A and 4B, together, these diagrams respectively illustrate an illumination system 100 includes a deformable illumination section 106 that delivers light to a larger area and wider illumination angle than the forward light emitting illuminators. The deformable section 106 can be configured in two ways to give the desired field of illumination and intensity of illumination in the field of interest. First, the sections 104 and 106 may be bent and shaped to a desired shape/configuration once the surgical field of interest has been established. Second, sections of the elongate section 106 may be masked or coated with a reflective coating to reflect light being emitted along the length of section 106 so that it is reflected back out the unmasked or uncoated sections along length of section 106. Sections 104 and 106 are made of the same material so light coupled from coupler 102 into section 104 is transmitted to section 106 out of which the light is emitted. Section 102 may be coated with a reflective material to prevent losses at the air/surface interface to ensure the most amount of light is transmitted to section 106 from the light source.

Figure 5A:
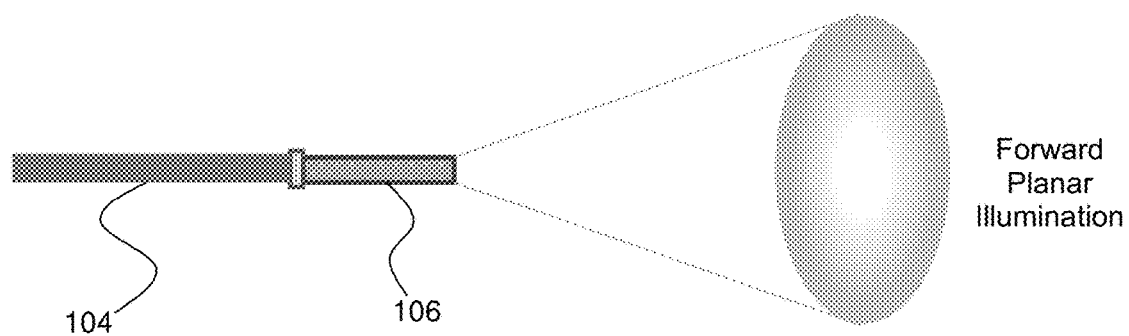
FIG. 5A is a diagram illustrating an embodiment of the lighting system similar to the system, as shown in FIGS. 4A and 4B, but having a coating over the elongate section so light is only emitted out the distal end of the elongate section to give forward planar illumination.

Referring to FIG. 5A, this diagram illustrates a lighting system comprising a coating disposed over the elongate section 106 so light is only emitted out the distal end of the elongate section to give forward planar illumination, in accordance with an embodiment of the present disclosure.

Figure 5B:
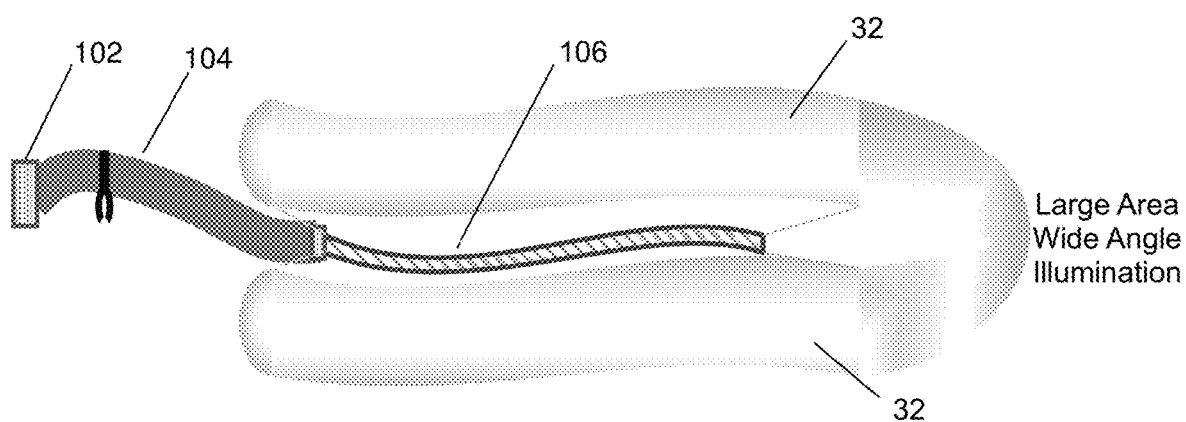
FIG. 5B is a diagram illustrating an embodiment of the lighting system similar to the system, as shown in FIGS. 4A and 4B, which is uncoated all along its length to give large area wide angle illumination.

Referring to FIG. 5B, this diagram illustrates a lighting system which is uncoated all along the length of flexible section 106 to give large area wide angle illumination, with the elongate light emitting section 106 shown nestled in the sulci 32 of a patient's brain, in accordance with an embodiment of the present disclosure.

Figure 6A:
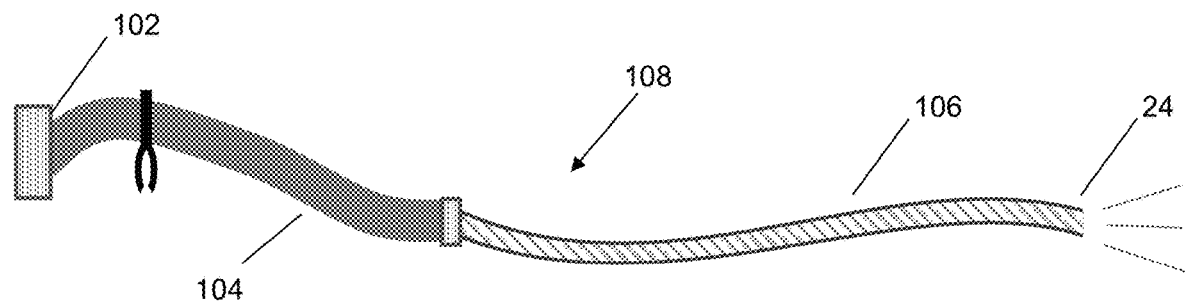
FIG. 6A is a diagram illustrating an embodiment of a lighting system.
Figure 6B:
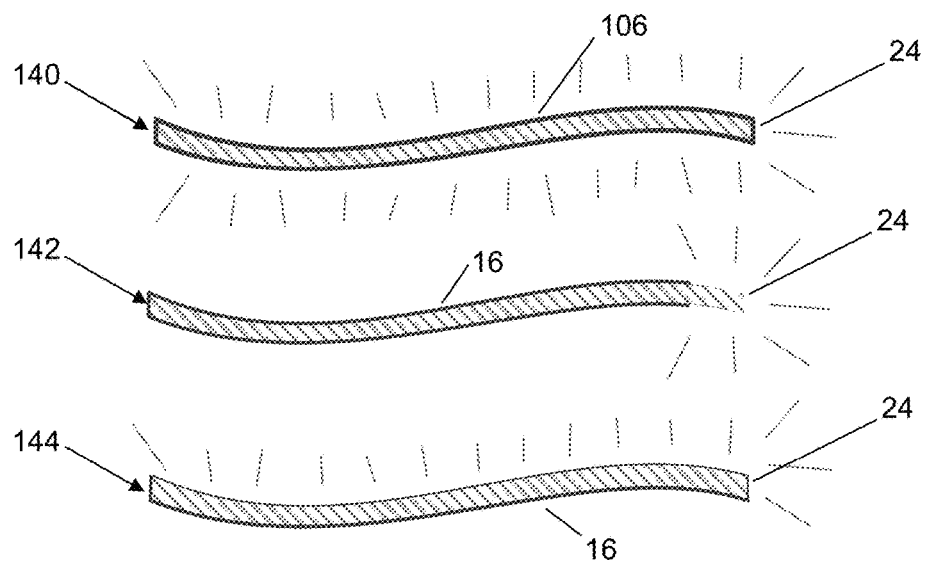
FIG. 6B is a diagram illustrating an embodiment of a lighting system.
Figure 6C:
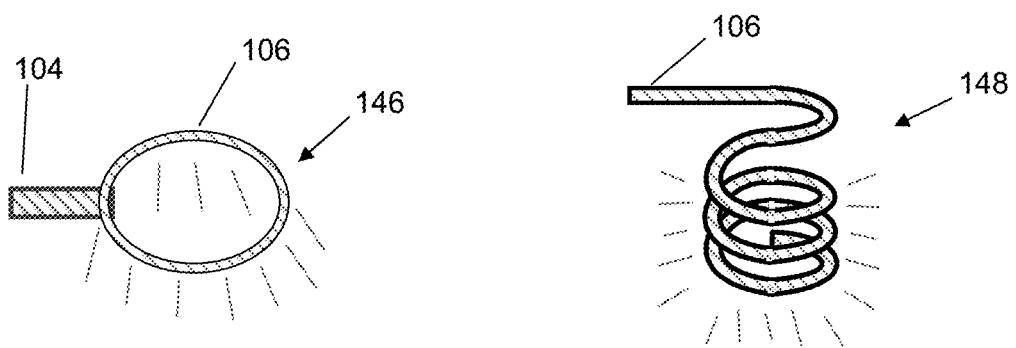
FIG. 6C is a diagram illustrating an embodiment of a lighting system.
Figure 6D:
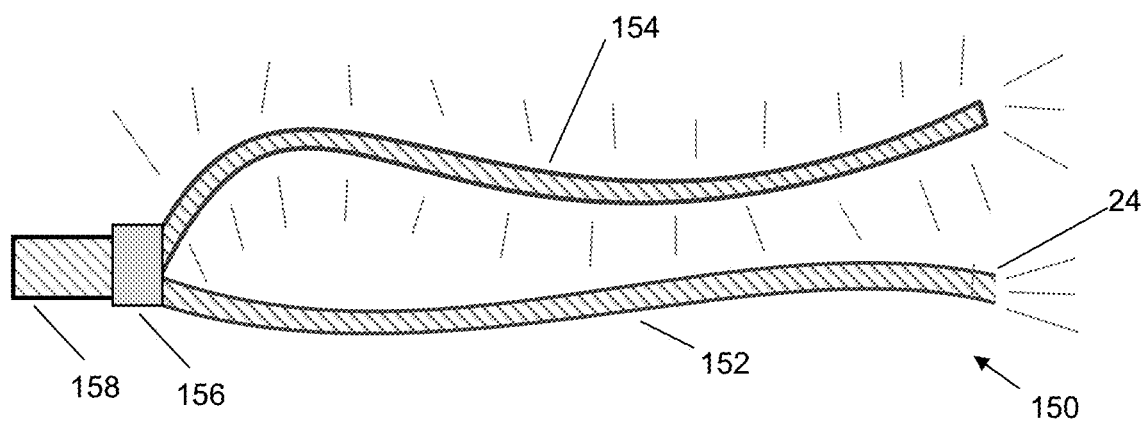
FIG. 6D is a diagram illustrating an embodiment of a lighting system.

Referring to FIGS. 6A through 6D, together, these diagrams respectively illustrate lighting systems, in accordance with embodiments of the present disclosure. In FIG. 6A, an embodiment of a lighting system 108 comprises an elongate section 106 coated with a reflective coating on the outer surface thereof so all light is reflected back into the body of section 106 and emitted from the distal end 24 to give forward planar illumination. In FIG. 6B, an embodiment of a lighting system 140 comprises an elongate section 106 which is uncoated along its length so that light is emitted all along its length and its distal end 24. In FIG. 6B, an embodiment of a lighting system 142 comprises an elongate section 106 which is coated along most of its length, but not all of its length, so that light is emitted at its distal end 24 and a short portion adjacent to the distal end 24. An embodiment of a lighting system 144 comprises an elongate section 106 which is coated along most of its length, but not totally circumferentially, so that light is emitted from one side of elongate section 106 and the emitted at its distal end 24. In FIG. 6C, an embodiment of a lighting system 146, left hand side, comprises an elongate section 106 shaped into a circular shape so that a circular area is illuminated. In FIG. 6C, an embodiment of a lighting system 148, right hand side, shows the elongate section 106 shaped into a coil, for example it may be shaped to coil around a surgical tool to illuminate the region around the tool. In FIG. 6D, an embodiment of a lighting system 150 comprises a deformable illuminator having two elongate sections 152 and 154 shaped with each having their proximal ends coupled with a light source 158 (an example of a light source being the end of an optical fiber bundle) by a coupler 156. The elongate section 154 is uncoated so light is emitted all along its length. The elongate section 152 is coated all around its circumference so light is only emitted at its distal end 24. Sections 152 and 154 are shaped independently of each other as required.

Figure 7A:
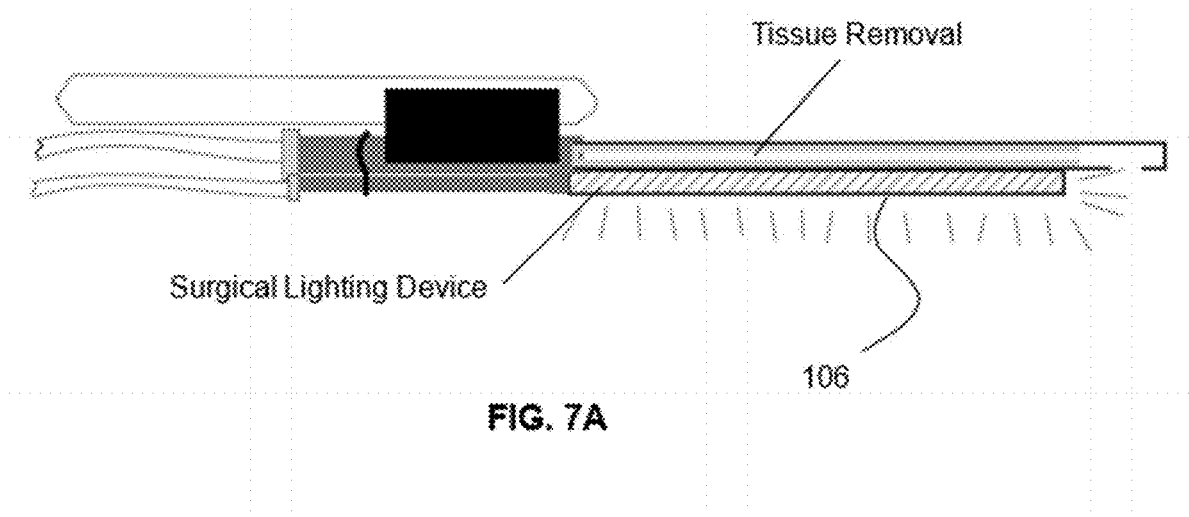
FIG. 7A is a diagram illustrating integrating an embodiment of the lighting system with a surgical tool.
Figure 7B:
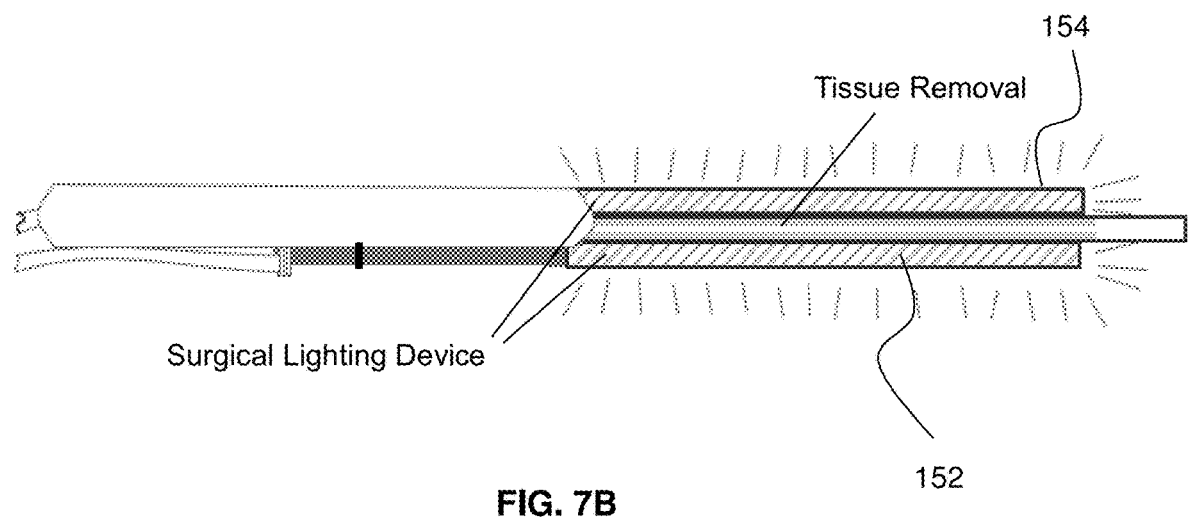
FIG. 7B is a diagram illustrating integrating another embodiment of the lighting system with a surgical tool.

Referring to FIGS. 7A and 7B, together, these diagrams respectively illustrate several different non-limiting exemplary embodiments of integrating the lighting system with a surgical tool, in accordance with embodiments of the present disclosure. In FIG. 7A, only one illuminator 106, as shown in FIG. 6B, is integrated along the length of a tissue removal tool. In FIG. 7B, an illuminator, as shown in FIG. 6D, has two elongate sections 152 and 154 attached to opposite sides of the tissue removal tool.

Figure 8:
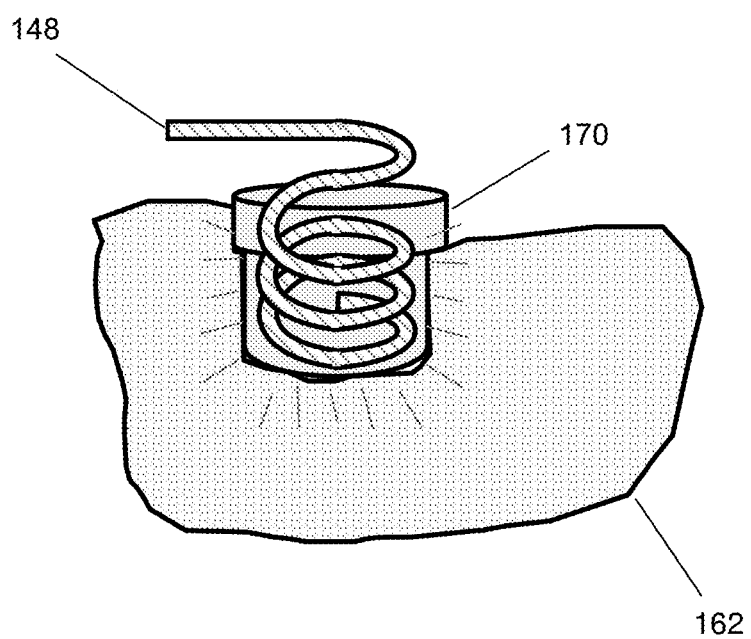
FIG. 8 is a diagram illustrating an exemplary embodiment of integrating the lighting system with an access port.

Referring to FIG. 8, this diagram illustrates integrating the coiled surgical lighting system 148, as shown in FIG. 6C, with an access port 170 inserted into tissue 162, in accordance with an embodiment of the present disclosure.

Figure 9:
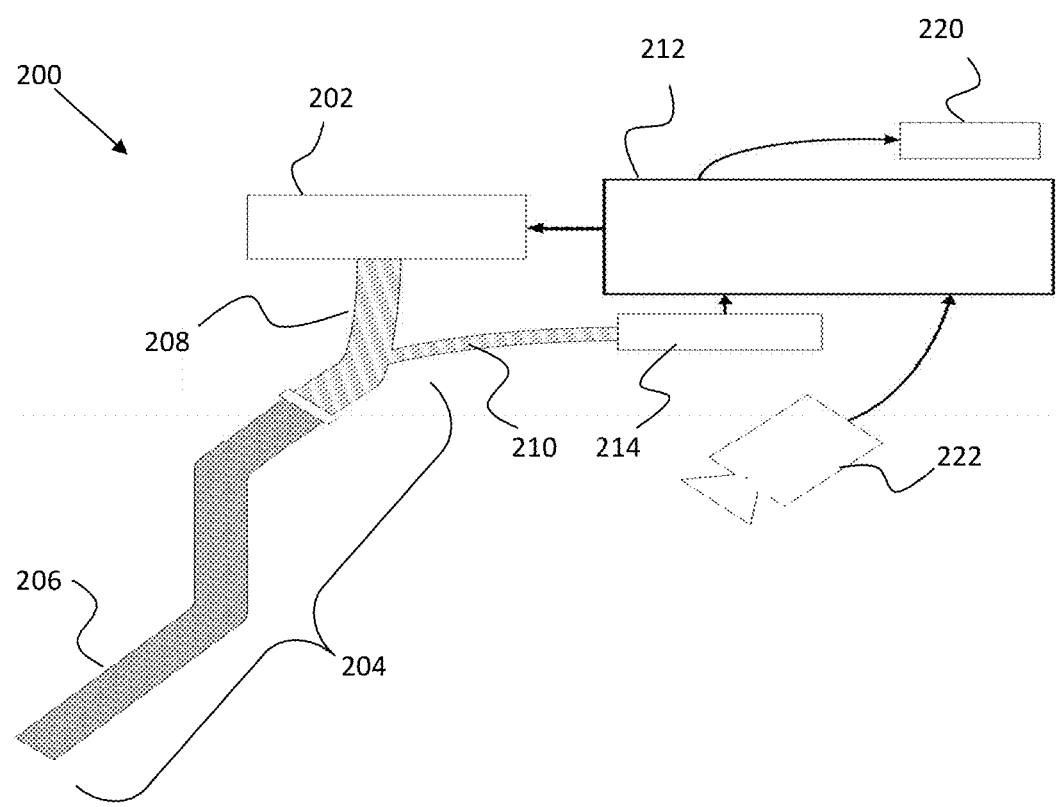
FIG. 9 is a block diagram illustrating a first embodiment of a feedback surgical lighting system.

Referring to FIG. 9, this diagram illustrates a feedback surgical lighting system shown generally at 200 includes a light source 202 in which its intensity and spectrum preferably are electrically controllable, in accordance with an embodiment of the present disclosure. For example, this could be achieved through the use of two electrically controlled motors (not shown). One motor can control the intensity of the output light through rotating a variable neutral density filter wheel or a variable aperture wheel, e.g., a wheel with different hole density in the tangential direction, set in the light path of the light source. The second motor can control the output light spectrum by rotating a spectrum adjuster set in the light path. One exemplary spectrum adjuster could be the one described in US20120236534 which for the purposes of the US is incorporated herein in its entirety. The spectrum adjuster includes a region of continuously-variable spectrum adjusting material, usable for adjusting the spectrum of light passing through the spectrum adjuster. The variable spectrum adjusting material may be a color-attenuating material, such as a filtering material, or it may be a wavelength-shifting material, such as a phosphor. The output light spectrum is adjusted based upon the relative positioning of the light source 202 and the spectrum adjuster which can be electrically controlled through a motor once the spectrum adjuster is set on a suitable axis.

Still referring to FIG. 9, the system 200 comprises a computer processor 212 and a spectrometer 214 connected to processor 212 that analyzes the color spectrum of the reflected light. The discussion above with respect to the computer 302 and memory 304 applies equally to computer processor 212 in system 200. The light source 202 is connected to the computer processor 212. A flexible surgical illuminator 204 has a flexible and shapeable distal section 206 comprises a scattering material, as discussed above, and a proximal fiber coupling comprising sections 208 and 210 which form a typical bifurcated fiber light pipe or fiber bundle. Coupling section 208 is optically coupled with the light source 202 for transmitting light from light source 202 to the flexible shapeable section 206 and coupling section 210 is configured for coupling the light source 202 to spectrometer 214.

Still referring to FIG. 9, the system 200 comprises a surgical camera 222 and a visual display 220 which are each connected to the computer processor 212. Spectrometer 214 analyzes the color spectrum of the reflected light received from the tissue sample through the flexible and shapeable distal section 206 and the coupling section 210. Computer processor 212 is programmed to take the input color spectrum from the spectrometer 214 and correct the color at the display 220 through comparing the input color spectrum with a standard reference or a color profile set for different surgical procedures. This color profile is programmable as it is typically different for different types of surgery, such as brain surgery versus arthroscopic surgery.

Figure 10:
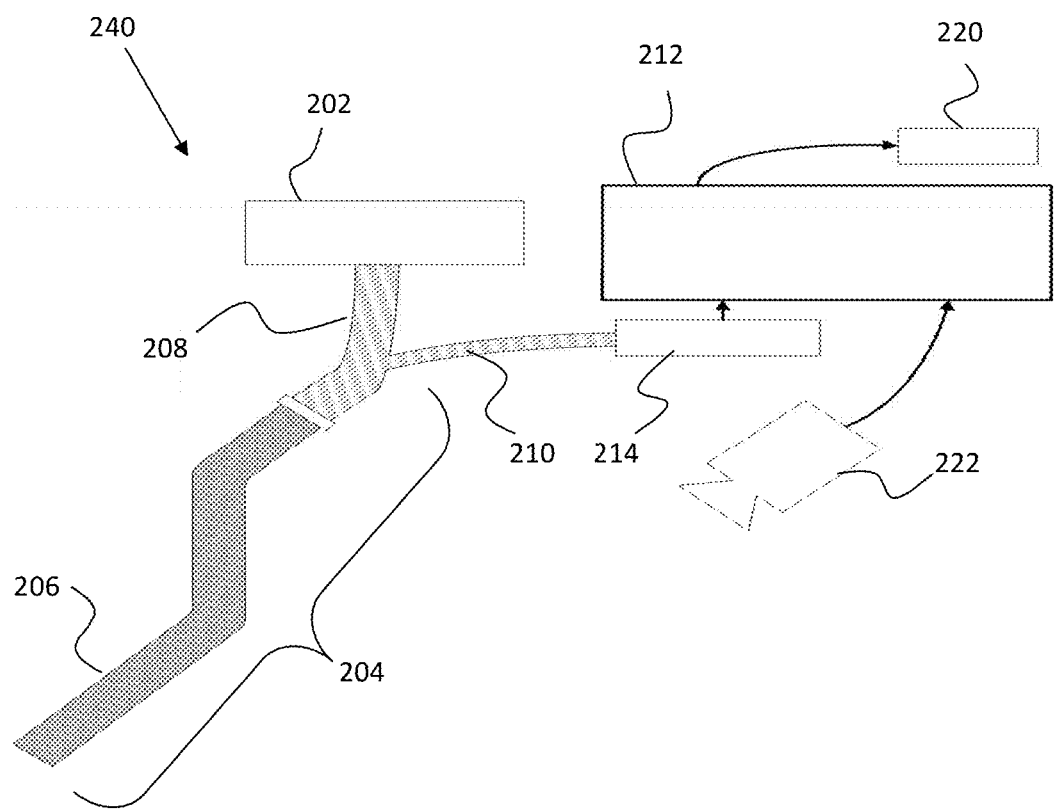
FIG. 10 is a block diagram illustrating a second embodiment of a feedback surgical lighting system.

Referring to FIG. 10, this diagram illustrates a system 240, having a similar configuration to system 200, as shown in FIG. 9, in accordance with an embodiment of the present disclosure. The difference is that system 240 does not have any communication between the processor 212 and the light source 202. In the case of system 240, the light source 202 does not need to have its intensity and spectrum electrically tunable. The intensity and color of the displayed image can be adjusted through color mapping in firmware or software stored in the processor 212. An advantage of system 200 is that the system 200 enables dynamic color correction and optimization so that the color correction and optimization can take into account the surrounding environment, tissue type, the illuminator type, position, number, and configurations, e.g., the deformed shape of the illuminator. Another advantage of the system 200 is that the system 200 enables switching between illumination mode for different images, such as white light imaging, narrow band illumination and fluorescence imaging for different dyes, through using only part of the light source spectrum or multi-spectral imaging mode by scanning through part of the source spectrum or even the entire source spectrum. In an example for tumour removal, the user can first utilize white light imaging for the initial part of the surgery. This initial part of the surgery might include, but not limited to, opening the surgical site and creating an access path to the potential location of the tumor. Then, the clinician can inject dye to the surgical area for fluorescent imaging. The dye could also be provided to the patient in other different ways including through drinking prior to the surgery.

Still referring to FIG. 10, fluorescent imaging is performed at the surgical area to identify the exact tumor location through switching the color profile at the processor 212 to that preset for fluorescent imaging for a particular dye. The fluorescent color profile then sets the illumination of the source from white light to one or multiple wavelengths or colors that match the excitation bands of the fluorescent dye. For example, for a fluorescent dye of PpIX, the light source is configured to illuminate narrowband light at only 408 nm, 510 nm, 543 nm, 583 nm, and 633 nm which are the excitation peaks of PpIX. This eliminates the need for an excitation filter for fluorescent imaging. Further, light emission can be focused at wavelengths or colors that are most efficient in exciting the fluorescent dye or less distracted to the user. Similarly, narrow band imaging can be performed through a preset profile. In the narrow band illumination profile, a narrow band wavelength or color is outputted at the source to show contrast for a particular type of tissue such as blood vessels with NIR light. Similarly, multi-spectral imaging could be performed through a preset profile. In the multi-spectral imaging profile, a narrow band wavelengths or color of the light at the source output is swept and the camera records a series of images each captured with a different band of wavelength. Processor then gives a false color to each of the capture images in the series and displays the series of images through a false color map.

Figure 11:
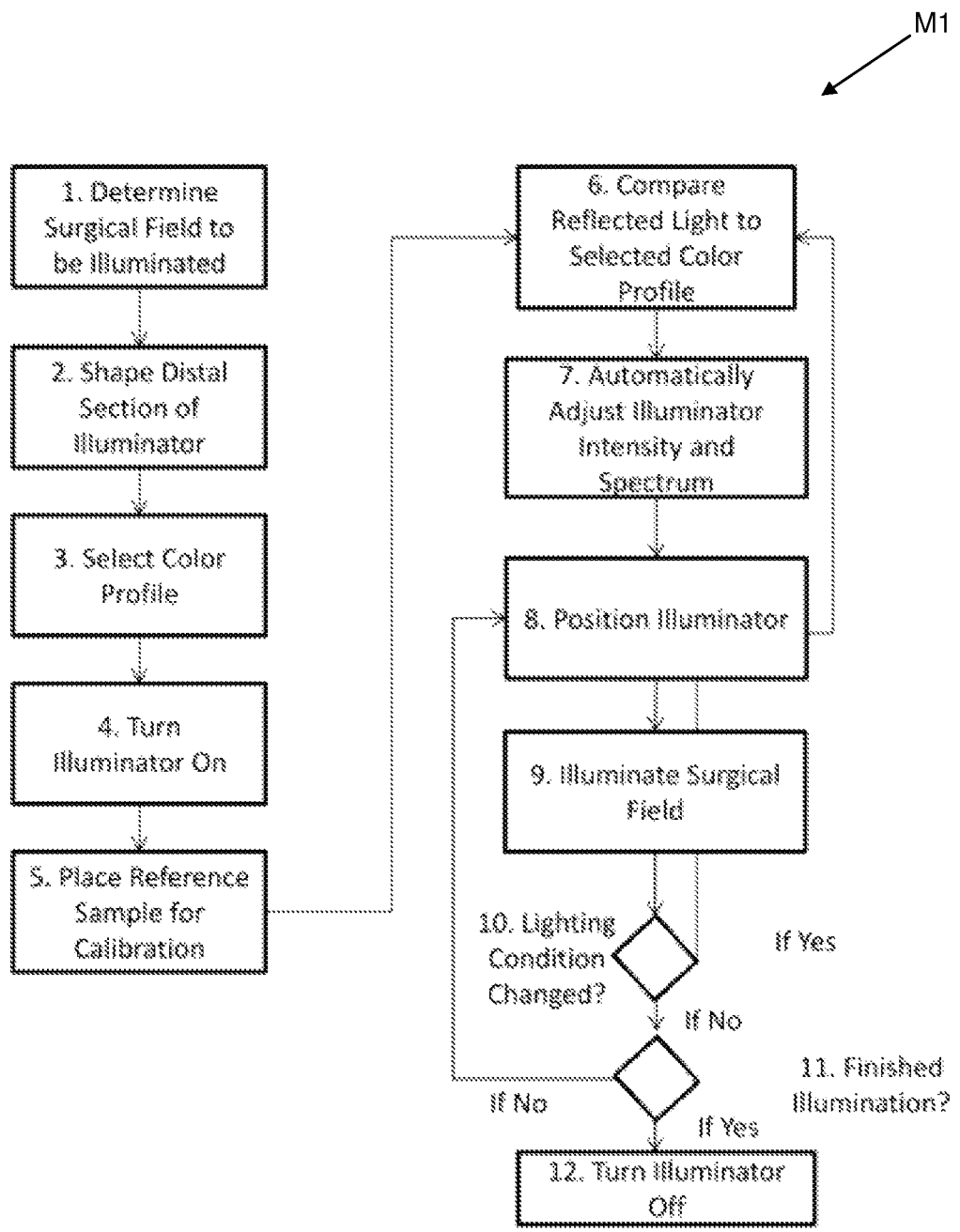
FIG. 11 is a flow chart illustrating general steps in a method of using the feedback lighting system.

Referring to FIG. 11, this flow chart illustrates general steps in a method M1 of using the feedback lighting system, in accordance with an embodiment of the present disclosure. First, in step 1 the user identifies the surgical area-of-interest in which illumination is required. Then, in step 2 the flexible and shapeable distal section 206 is shaped to provide the best illumination for the surgical field while maintaining the suitability of the surgical space for the surgeon to operate in. In step 3, the user selects a color profile that provides a suitable color scheme for the surgery being performed. Then, the illuminator is turned on in step 4; and, a reference sample is placed in front of the flexible and shapeable distal section 206 in step 5, where the light outputs, for color calibration. Light reflected from the reference sample is directed to the spectrometer 214 through coupling back into the flexible and shapeable distal section 206 and the coupling section 210. The spectrometer 214 then outputs the reflected light intensity and color spectrum to the processor 212. In step 6, at the processor 212, the reflected light intensity and color spectrum is then compared to a standard reference or color profile to derive a set of calibration coefficients that are used to map the input intensity and color spectrum to the color profile. This coefficient is then used to adjust the light source intensity and color spectrum in step 7 to give the desired light intensity and color spectrum.

Still referring to FIG. 11, after calibration, the flexible and shapeable distal section 206 is positioned to illuminate the surgical field in steps 8 and 9. As the lighting condition changes during the surgical procedure, the intensity and spectrum of the light reflected into the spectrometer 214 changes. The processor 212 then utilizes the changes in the intensity and spectrum to adjust the color mapping coefficients. The color adjustment could be made based on different methods. In step 10, the processor is programmed to determine if the lighting conditions have changed by comparison of the current lighting condition with the desired light intensity and color spectrum programmed above, and if no change has occurred and if in step 11 it is determined the procedure is finished the light source is turned off in step 12. Otherwise, if the lighting condition has changed as determined in step 10, and if the procedure still requires lighting then the illuminator is re-positioned as per step 8 and the procedure proceeds. Once the procedure is finished the illuminator is turned off in step 12.

Still referring to FIG. 11, one example method is based on a predictive method that utilizes the intensity per color detected to determine the lighting condition in the surgical field. For each lighting condition, a predetermined color mapping can be used to provide the best lighting condition and tissue contrast based on the selected color profile. The coefficient is then relayed to the light source 202 to adjust the illumination output dynamically to improve the lighting condition at the surgical field. For example, if the surgical field contains many fine blood vessels, the intensity of the red color can be increased to show a greater contrast in the surgical image.

Figure 12:
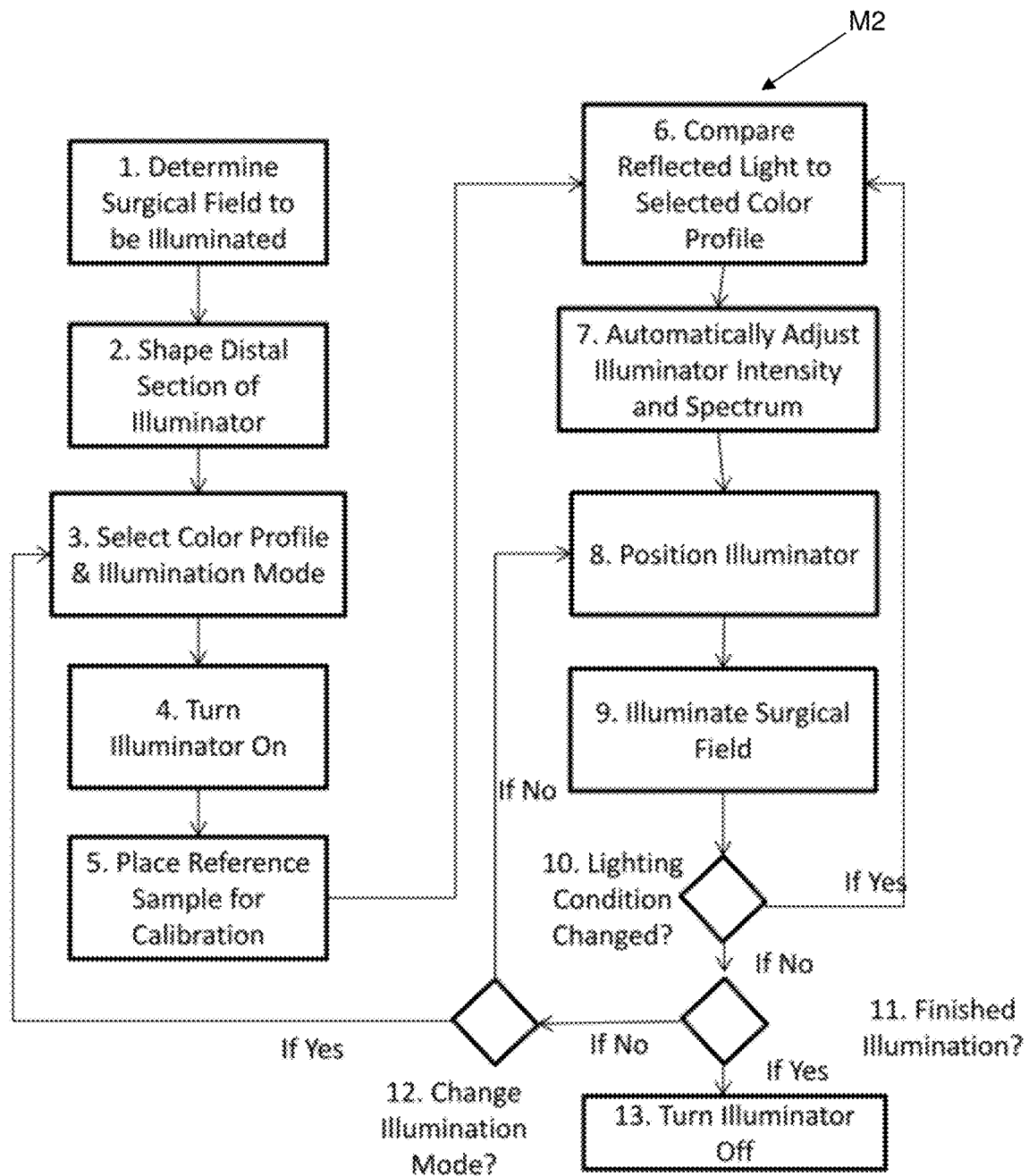
FIG. 12 is a flow chart illustrating general steps in another method of using the feedback lighting system.

Referring to FIG. 12, this flow chart illustrates a method M2 of using the feedback surgical system, in accordance with an embodiment of the present disclosure. In an example, if the surgical field contains many strong reflecting surfaces such as bones, the overall intensity can be reduced to prevent saturation in the surgical camera. If fluorescent imaging is required, a certain color can be set to illuminate the surgical field while turning the intensity for all the other color to low or zero. The user can also switch the color profile for cases such as switching between fluorescence imaging and white light imaging) during the surgical procedure without needing to change the illuminator and its position. The method M2 is similar to the method M1, except that an illuminator mode is selected in step 3 in which the user selects modes, such as, but not limited to, white light illumination mode or fluorescent illumination mode for a particular dye. In addition, the user can switch between the different illumination modes at step 12 until no more illumination is required and the illuminator is turned off in step 13.

Figure 13:
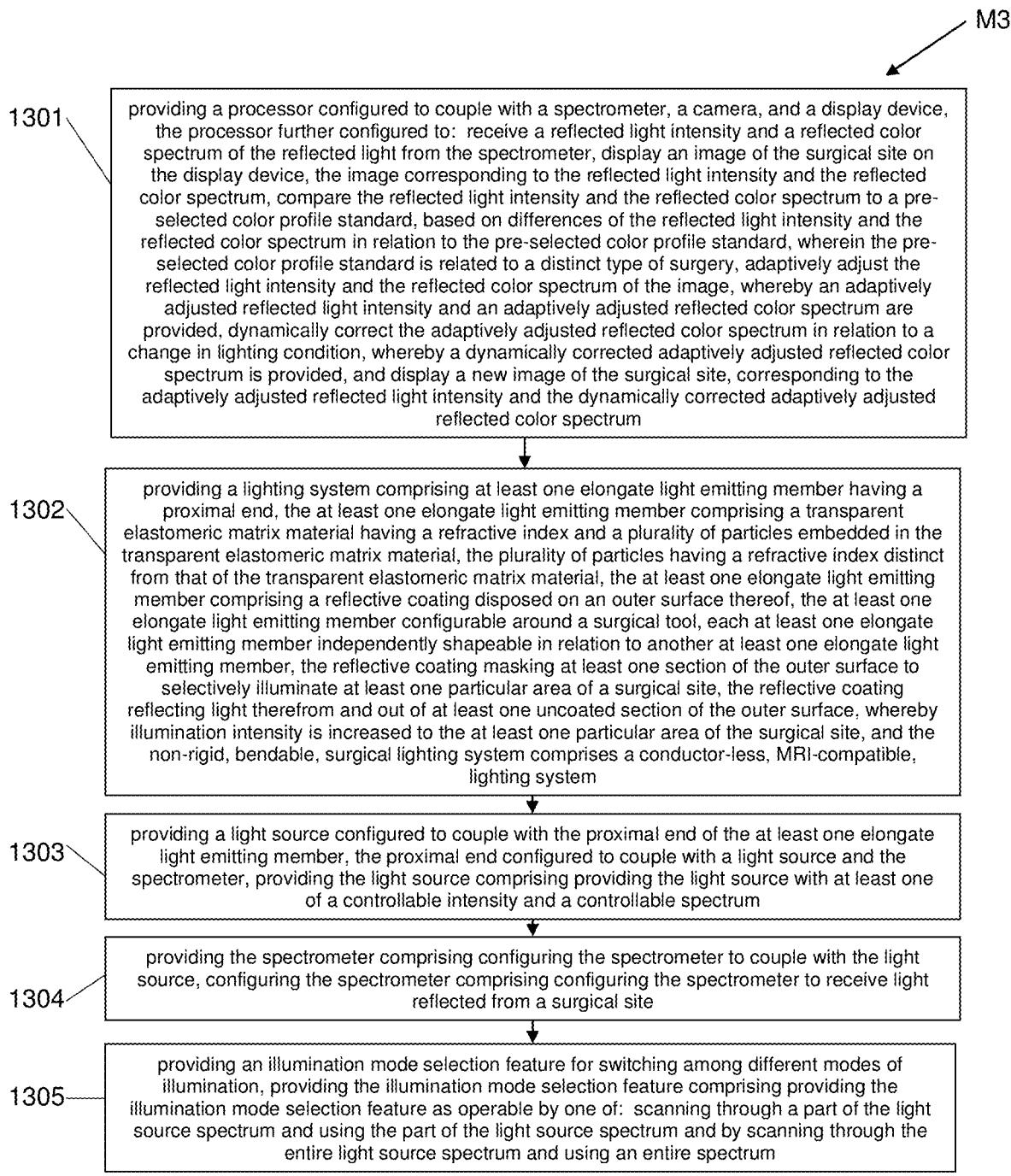
FIG. 13 is flow chart illustrating a method of providing a surgical lighting system, comprising providing a processor.

Referring to FIG. 13, this flow chart illustrates a method M3 of providing a surgical lighting system, comprising providing a processor, e.g., a processor 212, configured to couple with a spectrometer, e.g., a spectrometer 214, a camera, e.g., a camera 222, and a display device, e.g., a display 205, 211, 220, as indicated by block 1301, the processor further configured to: receive a reflected light intensity and a reflected color spectrum of the reflected light from the spectrometer, display an image of the surgical site on the display device, the image corresponding to the reflected light intensity and the reflected color spectrum, compare the reflected light intensity and the reflected color spectrum to a pre-selected color profile standard, based on differences of the reflected light intensity and the reflected color spectrum in relation to the pre-selected color profile standard, wherein the pre-selected color profile standard is related to a distinct type of surgery, adaptively adjust the reflected light intensity and the reflected color spectrum of the image, whereby an adaptively adjusted reflected light intensity and an adaptively adjusted reflected color spectrum are provided, dynamically correct the adaptively adjusted reflected color spectrum in relation to a change in lighting condition, whereby a dynamically corrected adaptively adjusted reflected color spectrum is provided, and display a new image of the surgical site, corresponding to the adaptively adjusted reflected light intensity and the dynamically corrected adaptively adjusted reflected color spectrum, in accordance with an embodiment of the present disclosure.

Still referring to FIG. 13, the method M3 further comprises: providing a lighting system comprising at least one elongate light emitting member having a proximal end, the at least one elongate light emitting member comprising a transparent elastomer matrix material having a refractive index and a plurality of particles embedded in the transparent elastomer matrix material, the plurality of particles having a refractive index distinct from that of the transparent elastomer matrix material, the at least one elongate light emitting member comprising a reflective coating disposed on an outer surface thereof, the at least one elongate light emitting member configurable around a surgical tool, each at least one elongate light emitting member independently shapeable in relation to another at least one elongate light emitting member, the reflective coating masking at least one section of the outer surface to selectively illuminate at least one particular area of a surgical site, the reflective coating reflecting light therefrom and out of at least one uncoated section of the outer surface, whereby illumination intensity is increased to the at least one particular area of the surgical site, and the non-rigid, bendable, surgical lighting system comprises a conductor-less, MRI-compatible, lighting system, as indicated by block 1302; providing a light source configured to couple with the proximal end of the at least one elongate light emitting member, the proximal end configured to couple with a light source and the spectrometer, providing the light source comprising providing the light source with at least one of a controllable intensity and a controllable spectrum, as indicated by block 1303; and providing the spectrometer comprising configuring the spectrometer to couple with the light source, configuring the spectrometer comprising configuring the spectrometer to receive light reflected from a surgical site, as indicated by block 1304, wherein providing the processor, as indicated by block 1301, further comprises configuring the processor to adaptively adjust the reflected light intensity and the reflected color spectrum of the image using at least one of firmware and software stored in relation to the computer processor, and wherein providing the processor, as indicated by block 1301, further comprises configuring the processor to enable dynamic color correction in relation to at least one of: a surrounding environment, an illuminator number, and an illuminator shape.

Still referring to FIG. 13, in the method M3, providing the light source, as indicated by block 1303, comprises configuring the light source to emit light and couple with the processor; and providing the processor, as indicated by block 1301, further comprises configuring the processor to adaptively adjust the reflected light intensity and the reflected color spectrum of the image by adaptively adjusting the controllable intensity and the controllable color spectrum of the light emitted by the light source. The method M3 further comprises providing an illumination mode selection feature for switching among different modes of illumination, providing the illumination mode selection feature comprising providing the illumination mode selection feature as operable by one of: scanning through a part of the light source spectrum and using the part of the light source spectrum and by scanning through the entire light source spectrum and using an entire spectrum. Providing the illumination mode selection feature, as indicated by block 1305, comprises providing the illumination mode selection feature for switching among the different modes of illumination comprising a white light illumination mode, a narrow band illumination mode, and a fluorescent illumination mode for a selected particular dye and a selected multi-spectral imaging mode.

Still referring to FIG. 13, in the method M3, the transparent elastomer matrix comprises at least one of an acrylate ester polymer and an acrylate ester copolymer; and the acrylate ester copolymer comprises an acrylate ester monomer and at least one monomer of a methacrylate ester, styrene, alpha-methyl styrene, vinyl acetate, methyl vinyl ketone, phenyl vinyl ketone and vinyl benzoate monomer, and wherein at least one of the acrylate ester polymer, the acrylate ester monomer, and the methacrylate ester comprises at last one of a methyl substituent, an ethyl substituent, a butyl substituent, a propyl substituent, a stearyl substituent, a lauryl substituent, a 2-ethylhexyl substituent, a cyclohexyl substituent, tetrahydrofurfuryl substituent, an aminoethyl substituent, a 2-hydroxyethyl substituent, a 3-hydroxypropyl substituent, a 3-chloro-2-hydroxypropyl substituent, and a trifluoroethyl substituent. The particles of the transparent material comprise at least one inorganic material of quartz glass, multicomponent glass, sapphire, and quartz. The difference in index of refraction between the transparent elastomer matrix and the particles of the transparent material is at least approximately 0.03.

Still referring to FIG. 13, in the method M3, the particles of the transparent material comprise a size greater than the wavelength of incident light by a factor of approximately 2 to approximately 10. The transparent material particles is blended in an amount of approximately 0.01 parts, by weight per 100 parts by weight of the transparent elastomer matrix, to approximately 10 parts by weight, per 100 parts by weight of the transparent elastomer matrix. The particles of the transparent material comprise at least one organic material of a polyamide, a polystyrene, a polymethyl methacrylate, a polycarbonate, a polyvinyl chloride, a polyvinylidene chloride, a polyvinyl acetate, a polyethylenevinyl acetate copolymer, a polyvinyl alcohol, a polyethylenepolyvinyl alcohol copolymer, a fluoride resin, a silicone resin, a polyisoprene rubber, a polybutadiene rubber, a styrene-butadiene copolymer, a butyl rubber, halogenated butyl rubber, a chloroprene rubber, an acrylic rubber, an EPDM, an acrylonitrile-butadiene copolymer, a fluoride rubber, a silicone rubber, an acrylonitrile-butadiene-styrene resin, an acrylonitrile-styrene copolymer resin, a styrene-butadiene copolymer, an acrylonitrile-EPDM-styrene terpolymer, a styrene-methyl methacrylate copolymer, methacrylic resin, epoxy resin, a polymethyl pentene, allyl diglycol carbonate resin, a spirane resin, amorphous polyolefin, a polyallylate, polysulfone, a polyallyl sulfone polyether sulfone, a polyether imide, polyimide, a polyethylene terephthalate, a diallyl phthalate, a polyester carbonate, paraffin, a polybutene, and a polyisobutylene. The lighting system is at least one of conductorless and MRI-compatible.

Referring back to FIGS. 1-13, deformability is an important aspect of this illumination system for surgical environments. This feature enables the illumination field to be shaped once a surgical region has been exposed to provide an irregular field of illumination as needed. Furthermore, this feature enables relative intensity control over the surgical field to focus light in multiple main areas while providing enough lighting in other areas for the surgeon to observe the field. This feature deformability may also be used with the optional feature of masking the section 106, to provide illumination directionality and intensity control.

Still referring back to FIGS. 1-13, the illumination system may be coupled to a surgical tool, such as an access port or a resection tool, to allow the illumination to focus on or follow the field of interest in which the surgeon is operating on. In addition, the illuminator(s) can be brought closer to the field of interest compared to conventional illumination systems in which the illuminator is coupled to the camera on top of the surgical field or just held on top of the surgical field. This allows the illuminator(s) to illuminate the entire surgical field with higher brightness.

Still referring back to FIGS. 1-13, other optical elements may be coupled to the elongate sections 106. For example, micro-lenses, focusing optics or polarization-controlled optics, e.g., polarizers, quarter wave-plates, are used in any combination to further focus or defocus the light to achieve different areas of illumination, different shapes of the illumination field and different intensities of brightness or illumination. The careful design of these optical components can further be used to minimize other unwanted effects such as shadows from surgical tools.

Still referring back to FIGS. 1-13, in addition, wavelength filters are added and positioned in front of the light emitted from the illuminator to provide wavelength selected illumination for a large field area with an unconventional field shape. This could be particularly useful for fluorescence imaging, multispectral imaging and hyperspectral imaging to focus the excitation light on a larger illumination field. Exemplary materials that may be used to produce the flexible, shape-able and deformable surgical lighting system disclosed herein are disclosed in U.S. Pat. No. 5,744,534, issued Apr. 28, 1998, which is incorporated herein in its entirety by reference. U.S. Pat. No. 6,591,049 describes other potential materials and method or producing light emitting materials, which is incorporated herein in its entirety by reference.

Still referring back to FIGS. 1-13, the materials used to make the flexible, shape-able and deformable surgical lighting are made by mixing and dispersing a transparent material in a transparent elastomer matrix having a glass transition temperature that is lower or substantially equal to room temperature, with the transparent material selected to have an index of refraction different from a refractive index of the matrix. The light scattering material is prepared by mixing with and dispersing in a transparent elastomer matrix material particles of a transparent material of a different refractive index than the matrix material. In an embodiment this may be achieved by mixing with and dispersing the transparent material in a monomer which is polymerized to form the transparent elastomer having the glass transition temperature lower than or equal to room temperature.

Still referring back to FIGS. 1-13, in another embodiment the material may be made by mixing a monomer into a transparent elastomer matrix having the glass transition temperature lower than or equal to room temperature and then inducing polymerization of the monomer into a polymer to produce the transparent material having a different index of refraction from the transparent elastomer. In another embodiment the light scattering material may be prepared by polymerizing at least two distinct monomers which have different reactivity and which when polymerized form transparent polymers having different indexes of refraction. One of the monomers upon polymerizing forms an elastomer matrix having the glass transition temperature of lower than or equal to room temperature.

Still referring back to FIGS. 1-13, in the resulting light scattering material has an optically inhomogeneous sea-island structure (the matrix forming the sea and the transparent particles the islands), so that light entering the light scattering material is scattered at the interface between the transparent material islands having different indexes of refraction due to refraction and reflection of light without a substantial loss by absorption because the light scattering material is entirely formed of the transparent materials. The incident light is efficiently scattered out of the material. Since the light scattering material is mainly formed of the elastomer matrix having a glass transition temperature of lower than room temperature, it is fully flexible and easy to handle and process at room temperature.

Still referring back to FIGS. 1-13, the transparent elastomer matrix may be selected from the group consisting of an acrylate ester polymer and an acrylate ester copolymer. The acrylate ester copolymer may comprise an acrylate ester monomer and a monomer selected from the group consisting of a methacrylate ester, styrene, alpha-methyl styrene, vinyl acetate, methyl vinyl ketone, phenyl vinyl ketone and vinyl benzoate monomer. The acrylate ester polymer, the acrylate ester monomer and the methacrylate ester contain a substituent selected from the group consisting of a methyl, ethyl, butyl, propyl, stearyl, lauryl, 2-ethylhexyl, cyclohexyl, tetrahydrofurfuryl, aminoethyl, 2-hydroxyethyl, 3-hydroxypropyl, 3-chloro-2-hydroxypropyl, and trifluoroethyl radical.

Still referring back to FIGS. 1-13, the term particles, as it refers to the transparent materials forming the islands the matrix sea, means transparent materials that may have spherical, ellipsoidal, rod, plate and or any other desired shape. The particles of transparent material may comprise an inorganic material selected from the group consisting of quartz glass, multicomponent glass, sapphire and quartz. Alternatively, the particles of transparent material may comprise an organic material selected from the group consisting of polyamides, polystyrene, polymethyl methacrylate, polycarbonate, polyvinyl chloride, polyvinylidene chloride, polyvinyl acetate, polyethylenevinyl acetate copolymers, polyvinyl alcohol, polyethylenepolyvinyl alcohol copolymers, fluoride resin, silicone resin, polyisoprene rubber, polybutadiene rubber, a styrene-butadiene copolymer, butyl rubber, halogenated butyl rubber, chloroprene rubber, acrylic rubber, EPDM, an acrylonitrile-butadiene copolymer, fluoride rubber, silicone rubber, acrylonitrile-butadiene-styrene resin, acrylonitrile-styrene copolymer resin, a styrene-butadiene copolymer, an acrylonitrile-EPDM-styrene terpolymer, a styrene-methyl methacrylate copolymer, methacrylic resin, epoxy resin, polymethyl pentene, allyl diglycol carbonate resin, spirane resin, amorphous polyolefin, polyallylate, polysulfone, polyallyl sulfone polyether sulfone, polyether imide, polyimide, polyethylene terephthalate, diallyl phthalate, polyester carbonate, paraffin, polybutene, and polyisobutylene.

Still referring back to FIGS. 1-13, the difference in index of refraction between the transparent elastomer matrix and the particles of the transparent material is at least 0.03, wherein the particles of the transparent material have a size greater than the wavelength of incident light by a factor of about 2 to about 10, the amount of the transparent material particles blended is about 0.01 to about 10 parts by weight per 100 parts by weight of the transparent elastomer matrix. Details on how to make the deformable and shape-able materials are disclosed in U.S. Pat. No. 5,744,534, which is herein incorporated by reference.

The specific embodiments, described above, have been shown by way of example. Understood is that these embodiments may be susceptible to various modifications and alternative forms. Further understood is that the claims are not intended to be limited to the particular forms disclosed, but, rather, to cover all modifications, equivalents, and alternatives falling within the spirit and scope of the present disclosure.

What is claimed:

1. A surgical lighting system, comprising a processor configured to couple with a spectrometer configured to receive light reflected from a surgical site, a camera, and a display device, the processor further configured to:
   receive a reflected light intensity and a reflected color spectrum of the reflected light from the spectrometer,
   display an image of the surgical site on the display device, the image corresponding to the reflected light intensity and the reflected color spectrum,
   compare the reflected light intensity and the reflected color spectrum to a pre-selected color profile standard,
   based on differences of the reflected light intensity and the reflected color spectrum in relation to the pre-selected color profile standard, wherein the pre-selected color profile standard is related to a distinct type of surgery, adaptively adjust the reflected light intensity and the reflected color spectrum of the image, whereby an adaptively adjusted reflected light intensity and an adaptively adjusted reflected color spectrum are provided,
   dynamically correct the adaptively adjusted reflected color spectrum in relation to a change in lighting condition, whereby a dynamically corrected adaptively adjusted reflected color spectrum is provided, and display a new image of the surgical site on the display device, the new image corresponding to the adaptively adjusted reflected light intensity and the dynamically corrected adaptively adjusted reflected color spectrum.

2. The system of claim 1, further comprising:

a lighting system comprising at least one elongate light emitting member having a proximal end, the at least one elongate light emitting member comprising a transparent elastomer matrix material having a refractive index and a plurality of particles embedded in the transparent elastomer matrix material, the plurality of particles having a refractive index distinct from that of the transparent elastomeric matrix material, the at least one elongate light emitting member comprising a reflective coating disposed on an outer surface thereof, the at least one elongate light emitting member configurable around a surgical tool, each at least one elongate light emitting member independently shapeable in relation to another at least one elongate light emitting member, the reflective coating masking at least one section of the outer surface to selectively illuminate at least one particular area of the surgical site, the reflective coating reflecting light therefrom and out of at least one uncoated section of the outer surface, whereby illumination intensity is increased to the at least one particular area of the surgical site, and the surgical lighting system comprises a non-rigid, bendable, conductor-less, MRI-compatible, lighting system;

a light source configured to couple with the proximal end of the at least one elongate light emitting member, the proximal end configured to couple with the light source and the spectrometer, the light source comprising at least one of a controllable intensity and a controllable spectrum; and the spectrometer configured to couple with the light source, the spectrometer configured to receive light reflected from the surgical site, wherein the processor is further configured to adaptively adjust the reflected light intensity and the reflected color spectrum of the image using at least one of firmware and software stored in relation to the computer processor, and wherein the processor is further configured to enable dynamic color correction in relation to at least one of: a surrounding environment, an illuminator number, and an illuminator shape.

3. The system of claim 2, wherein the light source is configured to emit light and couple with the processor, and wherein the processor is further configured to adaptively adjust the reflected light intensity and the reflected color spectrum of the image by adaptively adjusting the controllable intensity and the controllable color spectrum of the light emitted by the light source.

4. The system of claim 2, wherein the transparent elastomer matrix comprises at least one of an acrylate ester polymer and an acrylate ester copolymer, wherein the acrylate ester copolymer comprises an acrylate ester monomer and at least one monomer of a methacrylate ester, styrene, alpha-methyl styrene, vinyl acetate, methyl vinyl ketone, phenyl vinyl ketone and vinyl benzoate monomer, and wherein at least one of the acrylate ester polymer, the acrylate ester monomer, and the methacrylate ester each comprises at last one of a methyl substituent, an ethyl substituent, a butyl substituent, a propyl substituent, a stearyl substituent, a lauryl substituent, a 2-ethylhexyl substituent, a cyclohexyl substituent, tetrahydrofurfuryl substituent, an aminoethyl substituent, a 2-hydroxyethyl substituent, a 3-hydroxypropyl substituent, a 3-chloro-2-hydroxypropyl substituent, and a trifluoroethyl substituent.

5. The system of claim 2, wherein the particles of the transparent elastomer matrix material comprise at least one inorganic material of quartz glass, multicomponent glass, sapphire, and quartz, wherein the difference in index of refraction between the transparent elastomer matrix and the particles of the transparent elastomer matrix material is at least approximately 0.03, wherein the particles of the transparent material comprise a size greater than a wavelength of incident light by a factor of approximately 2 to approximately 10, wherein the transparent elastomer matrix material particles is blended in an amount of approximately 0.01 parts, by weight per 100 parts by weight of the transparent elastomer matrix, to approximately 10 parts by weight, per 100 parts by weight of the transparent elastomer matrix, wherein the particles of the transparent elastomer matrix material comprise at least one organic material of a polyamide, a polystyrene, a polymethyl methacrylate, a polycarbonate, a polyvinyl chloride, a polyvinylidene chloride, a polyvinyl acetate, a polyethylenevinyl acetate copolymer, a polyvinyl alcohol, a polyethylene-polyvinyl alcohol copolymer, a fluoride resin, a silicone resin, a polyisoprene rubber, a polybutadiene rubber, a styrene-butadiene copolymer, a butyl rubber, halogenated butyl rubber, a chloroprene rubber, an acrylic rubber, an EPDM, an acrylonitrile-butadiene copolymer, a fluoride rubber, a silicone rubber, an acrylonitrile-butadiene-styrene resin, an acrylonitrile-styrene copolymer resin, a styrene-butadiene copolymer, an acrylonitrile-EPDM-styrene terpolymer, a styrene-methyl methacrylate copolymer, methacrylic resin, epoxy resin, a polymethyl pentene, allyl diglycol carbonate resin, a spirane resin, amorphous polyolefin, a polyallylate, a polysulfone, a polyallyl sulfone polyether sulfone, a polyether imide, polyimide, a polyethylene terephthalate, a diallyl phthalate, a polyester carbonate, paraffin, a polybutene, and a polyisobutylene, and wherein the lighting system is at least one of conductorless and MRI-compatible.

6. The system of claim 1, further comprising an illumination mode selection feature for switching among different modes of illumination, the illumination mode selection feature operable by one of: scanning through a part of a light source spectrum and using the part of the light source spectrum and by scanning through the entire light source spectrum and using an entire spectrum.

7. The system of claim 6, wherein the different modes of illumination comprise a white light illumination mode, a narrow band illumination mode, and a fluorescent illumination mode for a selected particular dye and a selected multi-spectral imaging mode.

8. A method of providing a surgical lighting system, comprising providing a processor configured to couple with a spectrometer configured to receive light from a surgical site, a camera, and a display device, the processor further configured to:

receive a reflected light intensity and a reflected color spectrum of the reflected light from the spectrometer, display an image of the surgical site on the display device, the image corresponding to the reflected light intensity and the reflected color spectrum, compare the reflected light intensity and the reflected color spectrum to a pre-selected color profile standard, based on differences of the reflected light intensity and the reflected color spectrum in relation to the pre-selected color profile standard, wherein the pre-selected color profile standard is related to a distinct type of surgery, adaptively adjust the reflected light intensity and the reflected color spectrum of the image, whereby an adaptively adjusted reflected light intensity and an adaptively adjusted reflected color spectrum are provided, dynamically correct the adaptively adjusted reflected color spectrum in relation to a change in lighting condition, whereby a dynamically corrected adaptively adjusted reflected color spectrum is provided, and display a new image of the surgical site, corresponding to the adaptively adjusted reflected light intensity and the dynamically corrected adaptively adjusted reflected color spectrum.

9. The method of claim 8, further comprising:

providing the surgical lighting system comprising at least one elongate light emitting member having a proximal end, the at least one elongate light emitting member comprising a transparent elastomeric matrix material having a refractive index and a plurality of particles embedded in the transparent elastomeric matrix material, the plurality of particles having a refractive index distinct from that of the transparent elastomeric matrix material, the at least one elongate light emitting member comprising a reflective coating disposed on an outer surface thereof, the at least one elongate light emitting member configurable around a surgical tool, each at least one elongate light emitting member independently shapeable in relation to another at least one elongate light emitting member, the reflective coating masking at least one section of the outer surface to selectively illuminate at least one particular area of the surgical site, the reflective coating reflecting light therefrom out of at least one uncoated section of the outer surface, whereby illumination intensity is increased to the at least one particular area of the surgical site, and the surgical lighting system comprises a non-rigid, bendable, conductor-less, MRI-compatible lighting system;

providing a light source configured to couple with the proximal end of the at least one elongate light emitting member, the proximal end configured to couple with a light source and the spectrometer, providing the light source comprising providing the light source with at least one of a controllable intensity and a controllable spectrum; and providing the spectrometer comprising configuring the spectrometer to couple with the light source, configuring the spectrometer comprising configuring the spectrometer to receive light reflected from a surgical site;

wherein providing the processor further comprises configuring the processor to adaptively adjust the reflected light intensity and the reflected color spectrum of the image using at least one of firmware and software stored in relation to the processor, and wherein providing the processor further configuring the processor to enable dynamic color correction in relation to at least one of: a surrounding environment, an illuminator number, and an illuminator shape.

10. The method of claim 9, wherein providing the light source comprises configuring the light source to emit light and couple with the processor, and wherein providing the processor further comprises configuring the processor to adaptively adjust the reflected light intensity and the reflected color spectrum of the image by adaptively adjusting the controllable intensity and the controllable color spectrum of the light emitted by the light source.

11. The method of claim 9, wherein the transparent elastomer matrix comprises at least one of an acrylate ester polymer and an acrylate ester copolymer, wherein the acrylate ester copolymer comprises an acrylate ester monomer and at least one monomer of a methacrylate ester, styrene, alpha-methyl styrene, vinyl acetate, methyl vinyl ketone, phenyl vinyl ketone and vinyl benzoate monomer, and wherein at least one of the acrylate ester polymer, the acrylate ester monomer, and the methacrylate ester comprises at last one of a methyl substituent, an ethyl substituent, a butyl substituent, a propyl substituent, a stearyl substituent, a lauryl substituent, a 2-ethylhexyl substituent, a cyclohexyl substituent, tetrahydrofurfuryl substituent, an aminoethyl substituent, a 2-hydroxyethyl substituent, a 3-hydroxypropyl substituent, a 3-chloro-2-hydroxypropyl substituent, and a trifluoroethyl substituent.

12. The method of claim 9, wherein the particles of the transparent elastomer matrix material comprise at least one inorganic material of quartz glass, multicomponent glass, sapphire, and quartz, wherein the difference in index of refraction between the transparent elastomer matrix and the particles of the transparent elastomer matrix material is at least approximately 0.03, wherein the particles of the transparent material comprise a size greater than a wavelength of incident light by a factor of approximately 2 to approximately 10, wherein the transparent elastomer matrix material particles is blended in an amount of approximately 0.01 parts, by weight per 100 parts by weight of the transparent elastomer matrix, to approximately 10 parts by weight, per 100 parts by weight of the transparent elastomer matrix, wherein the particles of the transparent elastomer matrix material comprise at least one organic material of a polyamide, a polystyrene, a polymethyl methacrylate, a polycarbonate, a polyvinyl chloride, a polyvinylidene chloride, a polyvinyl acetate, a polyethylenevinyl acetate copolymer, a polyvinyl alcohol, a polyethylene-polyvinyl alcohol copolymer, a fluoride resin, a silicone resin, a polyisoprene rubber, a polybutadiene rubber, a styrene-butadiene copolymer, a butyl rubber, halogenated butyl rubber, a chloroprene rubber, an acrylic rubber, an EPDM, an acrylonitrile-butadiene copolymer, a fluoride rubber, a silicone rubber, an acrylonitrile-butadiene-styrene resin, an acrylonitrile-styrene copolymer resin, a styrene-butadiene copolymer, an acrylonitrile-EPDM-styrene terpolymer, a styrene-methyl methacrylate copolymer, methacrylic resin, epoxy resin, a polymethyl pentene, allyl diglycol carbonate resin, a spirane resin, amorphous polyolefin, a polyallylate, polysulfone, a polyallyl sulfone polyether sulfone, a polyether imide, polyimide, a polyethylene terephthalate, a diallyl phthalate, a polyester carbonate, paraffin, a polybutene, and a polyisobutylene, and wherein the lighting system is at least one of conductor-less and MRI-compatible.

13. The method of claim 8, further comprising providing an illumination mode selection feature for switching among different modes of illumination, providing the illumination mode selection feature comprising providing the illumination mode selection feature as operable by one of: scanning through a part of the light source spectrum and using the part of the light source spectrum and by scanning through the entire light source spectrum and using an entire spectrum.

14. The method of claim 13, wherein providing the illumination mode selection feature comprises providing the illumination mode selection feature for switching among the different modes of illumination comprising a white light illumination mode, a narrow band illumination mode, and a fluorescent illumination mode for a selected particular dye and a selected multi-spectral imaging mode.

15. A method of controlling illumination of a surgical site, comprising:
coupling a processor with a spectrometer, a camera, and a display device;
directing light emitted from at least one elongate light emitting and collecting member to the surgical site;
collecting light reflected from the surgical site by the at least one elongate light emitting and collecting member;
directing the collected reflected light into the spectrometer;
transmitting a reflected light intensity and a reflected color spectrum of the collected reflected light from the spectrometer to the processor;
displaying an image of the surgical site on the display device, the image corresponding to the reflected light intensity and the reflected color spectrum;
comparing the reflected light intensity and the reflected color spectrum to a pre-selected color profile standard;
based on differences of the reflected light intensity and the reflected color spectrum in relation to the pre-selected color profile standard, wherein the pre-selected color profile standard is related to a distinct type of surgery, adaptively adjusting the reflected light intensity and the reflected color spectrum of the image, thereby providing an adaptively adjusted reflected light intensity and an adaptively adjusted reflected color spectrum;
dynamically correcting the adaptively adjusted reflected color spectrum in relation to a change in lighting condition, thereby providing a dynamically corrected adaptively adjusted reflected color spectrum; and
displaying a new image of the surgical site, corresponding to the adaptively adjusted reflected light intensity and the dynamically corrected adaptively adjusted reflected color spectrum.

16. The method of claim 15, further comprising:
shaping a distal end of a flexible, bendable, surgical lighting member comprising the at least one elongate light emitting and collecting member having a proximal end, the at least one elongate light emitting and collecting member comprising a transparent elastomeric matrix material having a refractive index and a plurality of particles embedded in the transparent elastomeric matrix material, the plurality of particles having a refractive index distinct from that of the transparent elastomeric matrix material, the flexible, bendable, surgical lighting member comprising a reflective coating disposed on an outer surface thereof, the at least one elongate light emitting and collecting member configurable around a surgical tool, each at least one elongate light emitting member independently shapeable in relation to another at least one elongate light emitting member, the reflective coating masking at least one section of the outer surface to selectively illuminate at least one particular area of the surgical site, the reflective coating reflecting light therefrom and out of at least one uncoated section of the outer surface, whereby illumination intensity is increased to the at least one particular area of the surgical site, and the flexible, bendable, surgical lighting member comprises a conductor-less, MRI-compatible lighting system;
coupling a light source with the proximal end of the at least one elongate light emitting and collecting member; and
optically coupling the spectrometer to the light source;
wherein adaptively adjusting the reflected light intensity and the reflected color spectrum of the image comprises using at least one of firmware and software stored in relation to the processor, and
wherein dynamically correcting the reflected color spectrum further comprises dynamically correcting the reflected color spectrum in relation to at least one of: a surrounding environment, an illuminator number, and an illuminator shape.

17. The method of claim 16,
wherein the transparent elastomer matrix comprises at least one of an acrylate ester polymer and an acrylate ester copolymer,
wherein the acrylate ester copolymer comprises an acrylate ester monomer and at least one monomer of a methacrylate ester, styrene, alpha-methyl styrene, vinyl acetate, methyl vinyl ketone, phenyl vinyl ketone and vinyl benzoate monomer,
wherein at least one of the acrylate ester polymer, the acrylate ester monomer, and the methacrylate ester comprises at last one of a methyl substituent, an ethyl substituent, a butyl substituent, a propyl substituent, a stearyl substituent, a lauryl substituent, a 2-ethylhexyl substituent, a cyclohexyl substituent, tetrahydrofurfuryl substituent, an aminoethyl substituent, a 2-hydroxyethyl substituent, a 3-hydroxypropyl substituent, a 3-chloro-2-hydroxypropyl substituent, and a trifluoroethyl substituent,
wherein the particles of the transparent elastomer matrix material comprise at least one inorganic material of quartz glass, multicomponent glass, sapphire, and quartz,
wherein the difference in index of refraction between the transparent elastomer matrix and the particles of the transparent elastomer matrix material is at least approximately 0.03,
wherein the particles of the transparent elastomer matrix material comprise a size greater than a wavelength of incident light by a factor of approximately 2 to approximately 10,
wherein the transparent elastomer matrix material particles is blended in an amount of approximately 0.01 parts, by weight per 100 parts by weight of the transparent elastomer matrix, to approximately 10 parts by weight, per 100 parts by weight of the transparent elastomer matrix, wherein the particles of the transparent elastomer matrix material comprise at least one organic material of a polyamide, a polystyrene, a polymethyl methacrylate, a polycarbonate, a polyvinyl chloride, a polyvinylidene chloride, a polyvinyl acetate, a polyethylenevinyl acetate copolymer, a polyvinyl alcohol, a polyethylenepolyvinyl alcohol copolymer, a fluoride resin, a silicone resin, a polyisoprene rubber, a polybutadiene rubber, a styrene-butadiene copolymer, a butyl rubber, halogenated butyl rubber, a chloroprene rubber, an acrylic rubber, an EPDM, an acrylonitrile-butadiene copolymer, a fluoride rubber, a silicone rubber, an acrylonitrile-butadiene-styrene resin, an acrylonitrile-styrene copolymer resin, a styrene-butadiene copolymer, an acrylonitrile-EPDM-styrene terpolymer, a styrene-methyl methacrylate copolymer, methacrylic resin, epoxy resin, a polymethyl pentene, allyl diglycol carbonate resin, a spirane resin, amorphous polyolefin, a polyallylate, polysulfone, a polyallyl sulfone polyether sulfone, a polyether imide, polyimide, a polyethylene terephthalate, a diallyl phthalate, a polyester carbonate, paraffin, a polybutene, and a polyisobutylene, and wherein the lighting system is at least one of conductorless and MRI-compatible.

18. The method of claim 15, wherein coupling the light source comprises:

coupling the light source with the processor, and configuring the processor to adaptively adjust the reflected light intensity and the reflected color spectrum of the image by adaptively adjusting the controllable intensity and the controllable color spectrum of the light emitted by the light source.

19. The method of claim 15, further comprising switching among different modes of illumination using an illumination mode selection feature, switching comprising one of: scanning through the part of a light source spectrum and using a part of the light source spectrum and scanning through the entire light source spectrum and using an entire spectrum.

20. The method of claim 19, wherein the switching comprises switching among a white light illumination mode, a narrow band illumination mode, and a fluorescent illumination mode for a selected particular dye and a selected multi-spectral imaging mode.

* * * * *